US012247968B2

(12) United States Patent
Acedo et al.

(10) Patent No.: US 12,247,968 B2
(45) Date of Patent: Mar. 11, 2025

(54) METHODS AND SYSTEMS FOR GENERATING AND APPLYING AGRONOMIC INDICES FROM MICROBIOME-DERIVED PARAMETERS

(71) Applicant: Biome Makers Inc., West Sacramento, CA (US)

(72) Inventors: Alberto Acedo, Castile and León (ES); Héctor Ortega-Arranz, Valladolid (ES); Daniel Almonacid, Lafayette, CA (US); Adrian Ferrero, La Bañeza (ES); Beatriz Garcia Jimenez, Madrid (ES)

(73) Assignee: Biome Makers Inc., Davis, CA (US)

( * ) Notice: Subject to any disclaimer, the term of this patent is extended or adjusted under 35 U.S.C. 154(b) by 463 days.

(21) Appl. No.: 17/665,332

(22) Filed: Feb. 4, 2022

(65) Prior Publication Data

US 2022/0268756 A1    Aug. 25, 2022

Related U.S. Application Data

(60) Provisional application No. 63/182,498, filed on Apr. 30, 2021, provisional application No. 63/167,597, (Continued)

(51) Int. Cl.
| | | |
|---|---|---|
| *G01N 33/24* | (2006.01) | |
| *A01B 79/00* | (2006.01) | |
| *G06N 20/00* | (2019.01) | |

(52) U.S. Cl.
CPC ........... *G01N 33/24* (2013.01); *A01B 79/005* (2013.01); *G06N 20/00* (2019.01); *G01N 33/243* (2024.05); *G01N 33/245* (2024.05); *G01N 33/248* (2024.05)

(58) Field of Classification Search
CPC ...... G01N 20/00; G01N 15/01; G01N 15/019; G01N 2333/195–365;
(Continued)

(56) References Cited

U.S. PATENT DOCUMENTS

| | | |
|---|---|---|
| 9,771,795 B2 | 9/2017 | Knight et al. |
| 10,347,362 B2 | 7/2019 | Apte et al. |

(Continued)

FOREIGN PATENT DOCUMENTS

| | | |
|---|---|---|
| WO | 2020023808 A1 | 1/2020 |
| WO | 2020219932 A1 | 10/2020 |

OTHER PUBLICATIONS

Tkacz A, Hortala M, Poole PS. Absolute quantitation of microbiota abundance in environmental samples. Microbiome. Jun. 19, 2018; 6(1):110. (Year: 2018).*

(Continued)

*Primary Examiner* — Son T Le
*Assistant Examiner* — Brian Butler Geiss

(57) ABSTRACT

Inventions provided are designed to improve states of agriculture sites and crops, in relation to agricultural inputs and management practices. Some inventions covered are able to generate agronomic indices and execute actions in response to agronomic indices at an agriculture site. An example method includes receiving samples associated with the agriculture site; generating a sample dataset upon processing the samples with a set of sample processing operations; generating a set of microbiome-associated features upon performing a set of transformation operations upon the sample dataset, wherein the set of microbiome-associated features comprises taxonomic annotations, functional annotations and ecological indices; generating values of a set of agronomic indices based upon the set of microbiome-associated features; and executing an action for producing a desired (Continued)

outcome at the agriculture site, based upon the set of agronomic indices.

21 Claims, 9 Drawing Sheets

Related U.S. Application Data filed on Mar. 29, 2021, provisional application No. 63/167,628, filed on Mar. 29, 2021, provisional application No. 63/152,333, filed on Feb. 22, 2021.

(58) Field of Classification Search
CPC ... G01N 2333/37–40; G01N 2333/405; G01N 2333/41; G01N 2333/415–43; G01N 33/245; A01B 79/005; C12Q 1/00; C12Q 1/007; C12Q 1/008; C12Q 1/02; C12Q 1/04; C12Q 1/22; C12Q 1/25; C12Q 1/68; C12Q 1/6895; G16B 30/10; G16B 20/20; G16C 20/20; G16C 20/30; G16C 99/00

See application file for complete search history.

(56) References Cited

U.S. PATENT DOCUMENTS

| | | | |
|---|---|---|---|
| 10,395,355 | B2 | 8/2019 | Cohen |
| 10,827,669 | B2 | 11/2020 | Xu et al. |
| 11,028,449 | B2 | 6/2021 | Knight et al. |
| 2002/0103688 | A1 | 8/2002 | Schneider |
| 2005/0234691 | A1 | 10/2005 | Singh et al. |
| 2011/0137456 | A1 | 6/2011 | Koselka et al. |
| 2012/0109614 | A1 | 5/2012 | Lindores |
| 2014/0109249 | A1 | 4/2014 | Turner et al. |
| 2014/0120063 | A1 | 5/2014 | Stanford |
| 2015/0185196 | A1 | 7/2015 | Coram et al. |
| 2016/0217230 | A1 | 7/2016 | Mewes et al. |
| 2016/0290132 | A1 | 10/2016 | Knight et al. |
| 2016/0290918 | A1 | 10/2016 | Xu et al. |
| 2018/0213800 | A1 | 8/2018 | Djonovic et al. |
| 2018/0363031 | A1 | 12/2018 | Becares et al. |
| 2020/0194126 | A1 | 6/2020 | Lim et al. |
| 2021/0009483 | A1 | 1/2021 | Temme et al. |
| 2021/0092933 | A1 | 4/2021 | Spangenberg et al. |

OTHER PUBLICATIONS

Schmidt et al. "Agricultural management and plant selection interactively affect rhizosphere microbial community structure and nitrogen cycling", Microbiome vol. 7, Article No. 146, Jul. 11, 2019. Retrieved on Jul. 2, 2021. USA.

Girvan et al. "Community structure in social and biological networks", PNAS vol. 99, issue 12, Jun. 11, 2002. USA.

Van Klompenburg et al. "Crop yield prediction using machine learning: A systematic literature review", Computers and Electronics in Agriculture. 177(2020)105709, Aug. 18, 2020.

Konopka, Allan. "What is microbial community ecology", The ISME Journal. (2009) 3, 1223-1230. Aug. 6, 2009.

Netz et al. "Estimating computational limits on theoretical descriptions of biological cells", PNAS vol. 118, issue 6, Jan. 25, 2021. USA.

Veech, Joseph A. "A probablistic model for analysing species co-occurrence", Global Ecology and Biogeography, 2012.

Watts, et al. "Collective dynamics of 'small-world' networks". Nature vol. 393. Jun. 4, 1998.

Zele et al. "Ecology and evolution of facilitation among symbionts". Nature Communications (2018)9:4869.

International Search Report for PCT/US22/15348, mailed Jun. 8, 2022.

\* cited by examiner

Major Compounds

CARBON
Fixation: 87%
Aerobic respiration: 96%
Fermentation: 96%
Methanogenesis: 91%
Organic Matter Release: 70%

NITROGEN
Inorganic release: 96%
Inorganic consumption: 88%
Inorganic cycle health: 63%

PHOSPHORUS
Inorganic solubilization: 71%
Inorganic consumption: 90%
Organic assimilation: 90%

POTASSIUM
Solubilization: 71%
Consumption: 95%

Minor Compounds

Iron assimilation: 99%
Zinc transport equilibrium: 99%
Manganese transport equilibrium: 99%
Sulfur cycle equilibrium: 99%

Calcium transport: 94%
Copper export: 89%
Magnesium transport: 87%
Chlorine transport: 94%

FIGURE 2B

OUTPUT

| Soil | Crop | Variety | Time(s) |

SUMMARY

Biosustainability
Biodiversity: High
Functionality: Medium
Resistance: Very High

Health
Healthiness: Medium
Biocontrol: High
Hormone Production: Low
Stress Adaptation: Medium

Nutrition
C: Medium
N: High
P: Low
K: Low

Fungal Phylum Distribution

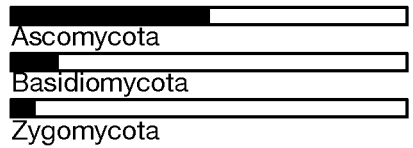

Ascomycota
Basidiomycota
Zygomycota

Bacterial Phylum Distribution

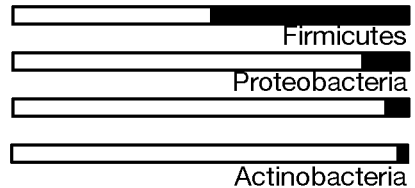

Firmicutes
Proteobacteria
Actinobacteria

Biosustainability
Biodiversity: High
Functionality: Medium
Resistance: Very High

Healthiness: Medium
2 Disease Risks Found

Verticillium Wilt: Medium risk
Fusarium Dry Rot: Low risk

Biocontrol
Fungicide agents: Very Low
Insecticide agents: Very High
Bactericide agents: none
Nematicide agents: none

Stress Adaptation
Exopolysaccharide production: Medium
Heavy metal solubilization: High
Salt tolerance: Low
Siderophore production: High
ACC deaminase: Medium
Salicylic acid: Medium
Abscisic acid: Medium

Hormone Production
Auxin Production: Low
Gibberellin Production: Medium
Cytokinin production: Very Low

FIGURE 2D

Major Compounds

CARBON
Fixation: High
Aerobic respiration: Medium
Fermentation: Low
Methanogenesis: High
Organic Matter Release: Medium NITROGEN
Inorganic release: High
Inorganic consumption: Medium
Inorganic cycle health: Medium PHOSPHORUS
Inorganic solubilization: Low
Inorganic consumption: Medium
Organic assimilation: Medium POTASSIUM
Solubilization: Low
Consumption: Medium Minor Compounds Iron assimilation: Medium
Zinc transport equilibrium: Medium
Manganese transport equilibrium: Medium
Sulfur cycle equilibrium: Medium Calcium transport: High
Copper export: Medium
Magnesium transport: Low
Chlorine transport: Medium

FIGURE 2E

CHEMICAL FERTILITY RATINGS

General Insights
Organic Matter: 3.5%
pH: 6.2
BpH: 4.65
ENR: 59lbs/acre

Texture:
Loam
Clay: 60%
Silt: 30%
Sand: 10%

Extractable Elements:
Nitrate-N: Very Low
Phosphorus: Very Low
Potassium: High
Calcium: Low Magnesium: High
Sulfur: Very High
Sulfate: Low

MACRO

Iron: Very High
Manganese: Very High
Copper: High

Zinc: Low
Boron: Very Low

MICRO

Detrimental Elements

Sodium: Very Low
Chloride: Very Low

CEC: 18.6 mew/100g
Base Saturation:
BSCa: 35.3%
BSH: 67.6%
BSK: 0.75%
BSMg: 34.5%
BSNa: 0.5%

FIGURE 2F

METHODS AND SYSTEMS FOR GENERATING AND APPLYING AGRONOMIC INDICES FROM MICROBIOME-DERIVED PARAMETERS

CROSS-REFERENCE TO RELATED APPLICATIONS

This application claims the benefit of U.S. Provisional Application No. 63/152,333 filed on 22 Feb. 2021, U.S. Provisional Application No. 63/167,597 filed on 29 Mar. 2021, U.S. Provisional Application No. 63/167,628 filed on 29 Mar. 2021, and U.S. Provisional Application No. 63/182,498 filed on 30 Apr. 2021, which are each incorporated in its entirety herein by this reference.

TECHNICAL FIELD

The disclosure generally relates to tools and systems executing methods for sampling and characterizing agricultural sites and crops, with actionable outcomes.

BACKGROUND

Agriculture ecosystems are human-managed ecosystems subject to various ecological rules, in relation to steady state scenarios and in response to various perturbations. Understanding the taxonomic, functional and ecological changes in soil microbial communities is a fruitful way to improve management practices, test various products and/or other agricultural inputs, evaluate sustainability, and therefore improve agriculture site productivity. Acquisition and processing of the appropriate data from agriculture-associated samples, development of models for characterization of ecosystem statuses, and generation of outputs and implementation of actions for maintaining such ecosystems, improving yields, improving crop nutrient content, improving soil carbon sequestration characteristics, identifying soil nutrient status and/or identifying disease risk are all areas of innovation in which the inventions described herein provide value.

BRIEF DESCRIPTION OF THE FIGURES

FIGS. 2A-2F depict exemplary outputs of the methods and/or systems described.

DESCRIPTION OF THE EMBODIMENTS

Figure 1:
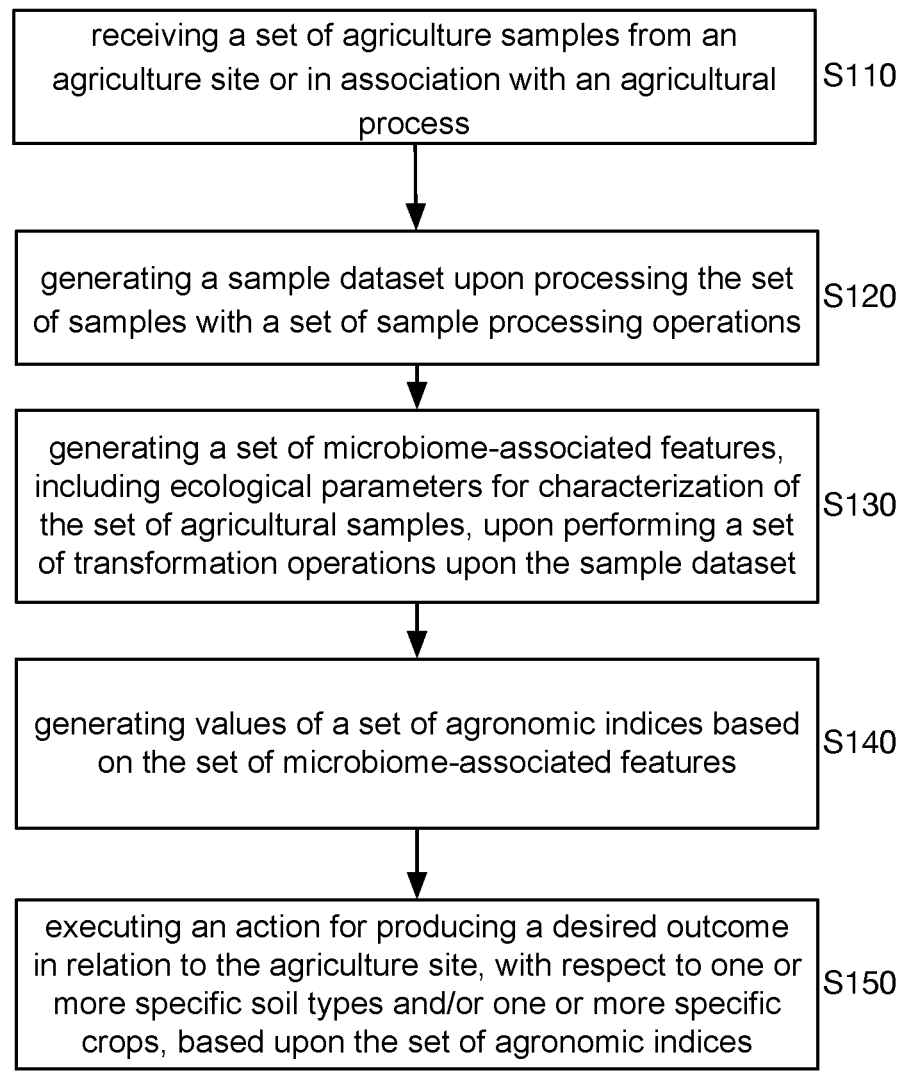
FIG. 1 depicts an embodiment of a workflow of a method for generating and applying agronomic indices.
Figure 2A:
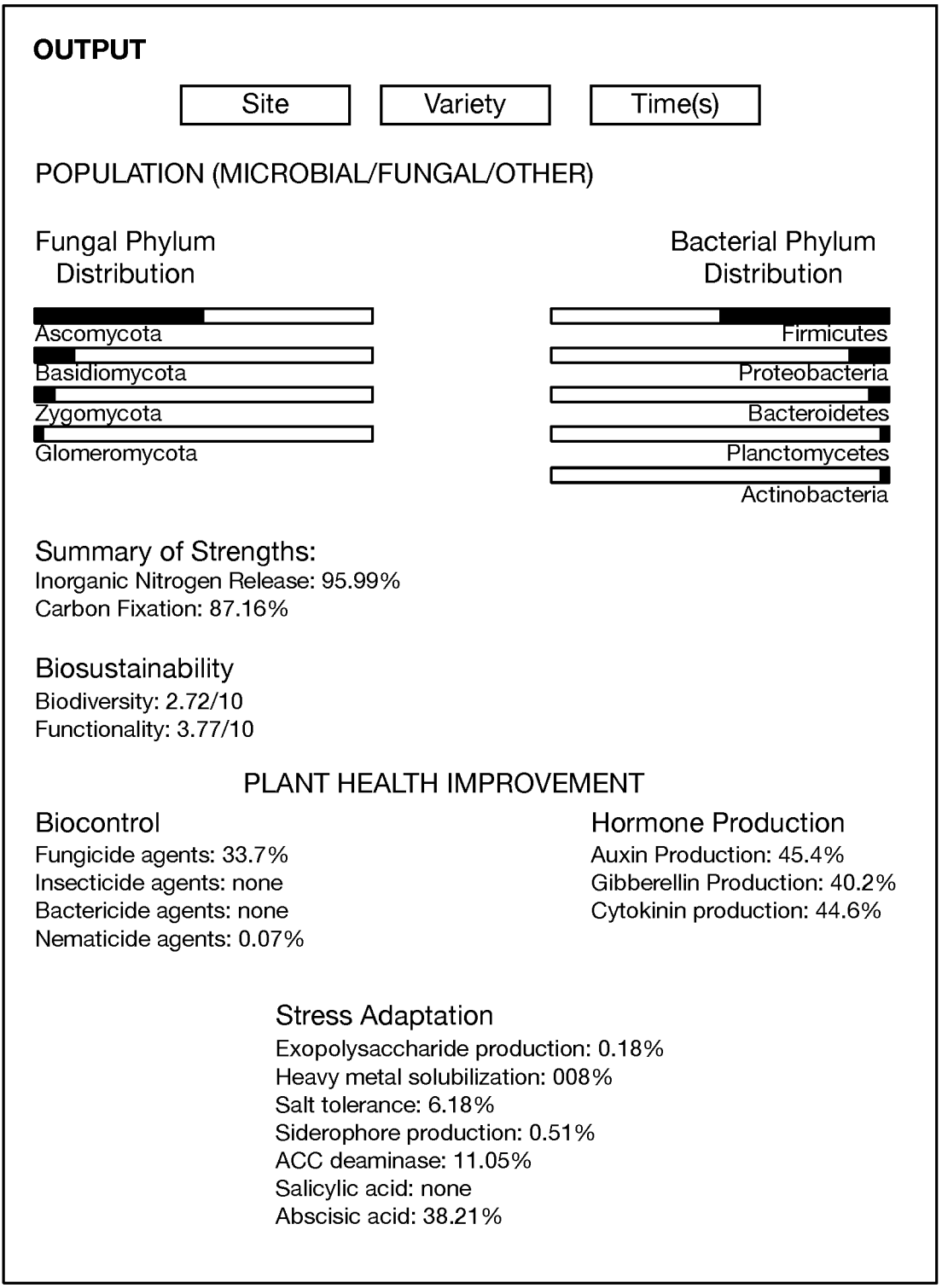
Figure 2C:
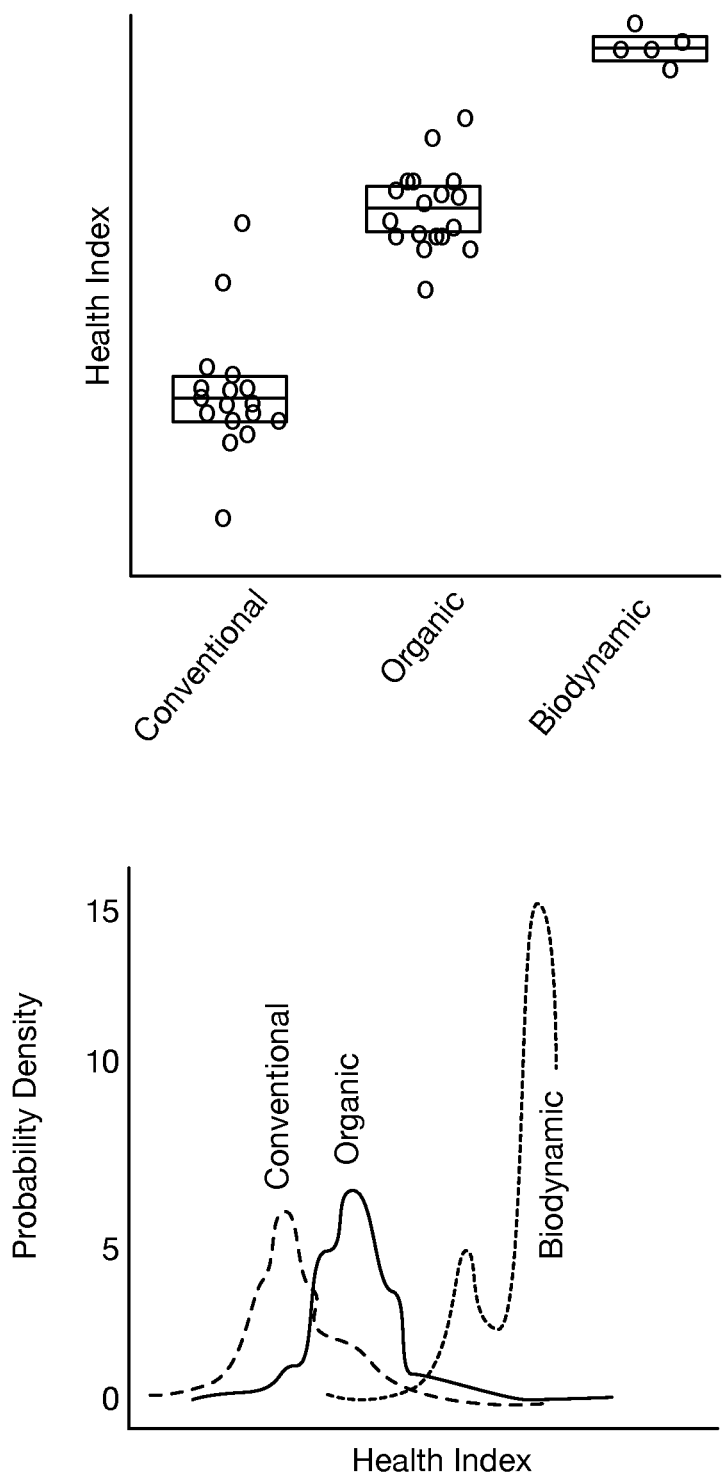

The following description of the embodiments (e.g., including variations of embodiments, examples of embodiments, specific examples of embodiments, other suitable variants, etc.) is not intended to be limited to these embodiments, but rather to enable any person skilled in the art to make and use.

1. Benefit(s)

The invention(s) cover embodiments, variations, and examples of systems and methods for generating agronomic indices for evaluation of agriculture sites and crops. Additional outputs of the invention(s) cover methods and systems for executing actions to maintain or improve states of agriculture sites and crops, in relation to agricultural inputs and management practices.

In embodiments, the invention(s) include systems and methods implementing structures and architecture for generating agronomic indexes from one or more annotation types, such as taxonomic annotations, functional annotations, ecological indices and/or other ecological annotations, which may or may not be combined with other annotation types and indices.

The invention(s) provide systems and methods for assessing soil microbiome populations and predicting various agriculture site and crop features, which are useful in downstream applications in relation to recommending or implementing various agriculture inputs and/or management practices to improve productivity or maintain health of the agriculture site.

In embodiments, the invention(s) include systems and methods for characterizing and implementing functional features associated with nutrient metabolic pathways based on inferred metagenomes (e.g., with respect to macronutrients and micronutrients) and/or species in relation to specific metabolic functions (i.e. phosphorus solubilizer microorganisms, other microorganisms).

In embodiments, the invention(s) include systems and methods for characterizing and implementing functional features related to plant growth promoters (PGPs), covering species known to produce phytohormones or stress tolerance molecules. Additionally or alternatively, the invention(s) can cover characterization and implementation of features based upon other functional organisms (e.g., biocontrol species).

In embodiments, the inventions include systems and methods for generating and implementing overall functional diversity indices, for generation of agronomic indices that can be used to maintain or improve outcomes related to crops/agricultural sites.

In embodiments, the invention(s) include systems and methods for characterizing and implementing ecological features associated with resilience, disease risk (e.g., crop-specific disease risk), health indices, sustainable productivity indices, and/or other combinations of taxonomic and functional indices, in relation to network and emergent properties.

In embodiments, the inventions include systems and methods for generating and implementing overall ecological indices, for generation of agronomic indices that can be used to maintain or improve outcomes related to crops/agricultural sites.

The invention(s) provide systems and methods for assessing soil microbiome functionality and predicting various agriculture site and crop features, which are useful in downstream applications in relation to recommending or implementing various agriculture inputs and/or management practices to improve productivity or maintain health of the agriculture site.

Additionally, in embodiments, the invention(s) described implement rapid processing of samples and data generated from sample processing, in order to extract insights related to predicted features of crops and agriculture sites, in a manner that cannot be practically performed by the human mind.

Additionally, in embodiments, the invention(s) provide methods for determining microbiome-associated or -derived properties (e.g., related to functional behavior and outputs of such organisms) in local microbial, fungal, and/or other organism communities, and to use them to assess the impact of different agricultural inputs and/or practices (e.g., agricultural management practices). Impact can be determined in relation to biosustainability, crop health improvement, crop nutritional characteristics, and/or other characteristics. For instance, the invention(s) can further provide methods and systems for evaluating, guiding, and/or executing implementation of various agricultural inputs and/or management practices for enhancement of yield (e.g., in relation to specific soil types and/or for specific crops) and/or improvement of agriculture site characteristics (e.g., with respect to health, with respect to sustainability).

In embodiments, the method(s) promote agro-ecosystem sustainability through assessment of soil organism functions, where the methods cannot be practically implemented by the human mind. The invention(s) thus process samples to extract patterns connecting sample ecosystem function in order to drive interventions based upon the impact of biotic (e.g., interspecies interactions, intraspecies interactions) and abiotic (e.g. climate or anthropogenic disturbances) factors. In practical applications, the methods can be used to restore soil functionality, predict yields, manage crop vulnerabilities, optimize their farming practices, and improve the sustainability of agricultural sites. Additionally or alternatively, the inventions can guide or inform management practices in relation to effects on soil carbon sequestration.

Additionally, the inventions described provide systems and a platform including architecture for agriculture sample extraction and processing, which provide improved tools for monitoring, forecasting, and responding to events (e.g., changes in productivity, events associated with management practices, environmental perturbations, product-induced perturbations, etc.) associated with one or more agricultural sites. Additionally or alternatively, the inventions can assess implementation of a plant variety and/or a seed variety at an agriculture site.

Additionally, the inventions apply outputs of the analyses to effect one or more actions (e.g., treatments) to maintain or improve the natural ecological site conditions, thereby providing practical applications of the method(s) and models involved.

Additionally, the inventions involve collection of samples from various agricultural sites, processing of samples to extract data features, application of one or more transformations to the data features to generate modified digital objects, create improved training data sets for machine learning/classification algorithms, and iteratively train the machine learning/classification algorithms, such that agriculture site statuses can be returned upon processing subsequent samples hitherto unseen by the algorithm.

Additionally or alternatively, the invention(s) can confer any other suitable benefit in any crop.

1.1 Definitions

The terms microbiome, microbiome information, microbiome data, microbiome population, microbiome panel and similar terms are used in the broadest possible sense, unless expressly stated otherwise, and would include: a census of currently present microorganisms, both living and non-living, which may have been present months, years, millennia or longer; a census of components of the microbiome other than bacteria and archaea (e.g., viruses, microbial eukaryotes, etc.); population studies and characterizations of microorganisms, genetic material, and biologic material; a census of any detectable biological material; and information that is derived or ascertained from genetic material, biomolecular makeup, fragments of genetic material, DNA, RNA, protein, carbohydrate, metabolite profile, fragment of biological materials and combinations and variations of these.

As used herein, the terms real-time microbiome data or information includes microbiome information that is collected or obtained at a particular setting or stage of an agricultural process for one or more agricultural sites.

As used herein, the terms derived microbiome information and derived microbiome data are to be given their broadest possible meaning, unless specified otherwise, and includes any real-time, microbiome information that has been computationally linked or used to create a relationship.

As used herein, the terms predictive microbiome information and predictive microbiome data are to be given their broadest possible meaning, unless specified otherwise, and includes information that is based upon combinations and computational links or processing of historic, predictive, real-time, and derived microbiome information, data, and combinations, variations and derivatives of these, which information predicts, forecasts, directs, or anticipates a future occurrence, event, state, or condition in the industrial setting, or allows interpretation of a current or past occurrence.

Real time, derived, and predicted data can be collected and stored, and thus, become historic data for ongoing or future decision-making for a process, setting, or application.

"Nucleic acid," "oligonucleotide," and "polynucleotide" refer to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. The term nucleic acid is used interchangeably with gene, cDNA, and mRNA encoded by a gene.

The term "microbiome", as used herein, refers to the ecological community of commensal, symbiotic, or pathogenic microorganisms in a sample.

The term "genome" as used herein, refers to the entirety of an organism's hereditary information that is encoded in its primary DNA sequence. The genome includes both the genes and the non-coding sequences. For example, the genome may represent a microbial genome or a mammalian genome.

Reference to "DNA region" should be understood as a reference to a specific section of genomic DNA. These DNA regions are specified either by reference to a gene name or a set of chromosomal coordinates. Both the gene names and the chromosomal coordinates would be well known to, and understood by, the person of skill in the art. In general, a gene can be routinely identified by reference to its name, via which both its sequences and chromosomal location can be routinely obtained, or by reference to its chromosomal coordinates, via which both the gene name and its sequence can also be routinely obtained.

Reference to each of the genes/DNA regions detailed above should be understood as a reference to all forms of these molecules and to fragments or variants thereof. As would be appreciated by the person of skill in the art, some genes are known to exhibit allelic variation or single nucleotide polymorphisms. SNPs encompass insertions and deletions of varying size and simple sequence repeats, such as dinucleotide and trinucleotide repeats. Variants include nucleic acid sequences from the same region sharing at least 90%, 95%, 98%, 99% sequence identity i.e. having one or more deletions, additions, substitutions, inverted sequences etc. relative to the DNA regions described herein. Accordingly, the present invention should be understood to extend to such variants which, in terms of the present applications, achieve the same outcome despite the fact that minor genetic variations between the actual nucleic acid sequences may exist between different bacterial strains. The present invention should therefore be understood to extend to all forms of DNA which arise from any other mutation, polymorphic or allelic variation.

The term "sequencing" as used herein refers to sequencing methods for determining the order of the nucleotide bases—adenine, guanine, cytosine, and thymine—in a nucleic acid molecule (e.g., a DNA or RNA nucleic acid molecule).

The term "barcode" as used herein, refers to any unique, non-naturally occurring, nucleic acid sequence that may be used to identify the originating source of a nucleic acid fragment.

A "computer-readable medium", is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

2. Method for Generating Agronomic Indices

As shown in FIG. 1, an embodiment of a method 100 for generating agronomic indices can include: receiving a set of agriculture samples associated with the agriculture site (e.g., from an agriculture site or in association with an agricultural process) S110; generating a sample dataset upon processing the set of samples with a set of sample processing operations S120; generating a set of microbiome-associated features, including taxonomic annotations, functional annotations, and/or ecological indices for characterization of the set of agricultural samples, upon performing a set of transformation operations upon the sample dataset S130; and generating values of a set of agronomic indices based on the set of microbiome-associated features S140. In some variations, the method 100 can additionally or alternatively include executing an action for producing a desired outcome in relation to the agriculture site, with respect to one or more specific soil types and/or one or more specific crops, based upon the set of agronomic indices S150.

The method 100 functions to generate taxonomic annotations, functional annotations, ecological indices, and/or other microbiome-associated features for generation of agronomic indices, which can be used to characterize aspects of an agricultural site and/or crops associated with the agricultural site. The method 100 implements novel steps for processing samples and data from such samples, in order to improve outcomes and practices. As such, the method 100 can generate insights using processes with improved efficiency and efficacy. Variations of the methods described can be implemented for various crop types, soil types, agriculture site locations, and/or other factors.

Furthermore, in downstream applications, refinement of models, system architecture, and sample processing techniques can be used to guide testing of, recommendation of, and/or implementation of (e.g., using automated or manual systems/devices) agricultural inputs, products for use, and management practices, in order to improve desired outcomes (e.g., in relation to nutrients, in relation to growth promotion, in relation to biocontrol, in relation to stress response, in relation to mitigating disease risk, in relation to yield, in relation to agriculture site health, in relation to sustainability, etc.). As such, the method(s) can provide steps for monitoring, controlling, and analyzing agriculture activities, with practical applications in food production, viticulture, bio-fuel production, and other agricultural activities.

The method(s) described can be implemented by systems and platforms described in Section 3 below. Additionally or alternatively, the method(s) described can be implemented by embodiments, variations, and examples of systems described in U.S. application Ser. No. 17/119,972 filed on 11 Dec. 2020 and U.S. application Ser. No. 17/587,016 filed on 28 Jan. 2022, which are each herein incorporated in its entirety by this reference.

2.1 Methods—Sample Reception and Sample Processing

Block S110 recites: receiving a set of agriculture samples from an agriculture site or in association with an agricultural process, and Block S120 recites: generating a sample dataset upon processing the set of samples with a set of sample processing operations. Blocks S110 and S120 function to process raw sample material with one or more operations, thereby generating base data from which features can be extracted in subsequent portions of the method.

Samples can be received from various portions of the agriculture site(s) and/or states of processing of crops or other products derived from the agriculture site. In embodiments, samples can be extracted from soil, another substrate, water used in agriculture, from various portions of crops, from organisms interacting with crops (e.g., parasites, other symbiotic organisms, etc.), from consumable products (e.g., food, beverages, supplements, etc.) derived from crops, from other surfaces (e.g., conduits used to deliver water or nutrients to crops, etc.), and/or from other suitable sampling sites. The samples can include solid samples (e.g., soil, sediment, rock, food samples). The samples can additionally or alternatively include liquid samples (e.g., surface water, sub-surface water, other liquids derived from crops, consumable products derived from crops, crop-derived products at various stages of processing or fermentation, etc.). The samples can additionally or alternatively include gas samples (e.g., samples from gases obtained from a greenhouse, gases produced during processing of crops or crop-derived products, etc.). Samples can be taken from crop portions (e.g., reproductive portions, petals, leaves, fruits, roots, trunks, flowers, pollen, etc.) and/or from crops in various states of health (e.g., healthy states, distressed states, diseased states, etc.).

Sample volumes can range from 0.01 grams to 1 kilogram (or greater than 1 kilogram, less than 0.01 gram). Additionally or alternatively, sample volumes can range from 1 microliter to 1 liter (or greater than 1 liter, less than 1 microliter).

Samples from different portions of the agriculture site, different portions of a crop, different portions or stages of a product being produces, and/or different sources can be combined in Block Silo.

In relation to Block Silo, sample reception/collection can be performed using equipment (e.g., machinery, robotic apparatus configured to traverse an agricultural site in coordination with retrieval of the set of agriculture samples, other apparatus) and/or manually. In variations, sample reception/collection performed in Step S110 can use any one or more of: an instrument (e.g., scoop for soil, sharp instrument for extracting a portion of a crop specimen, etc.), a permeable substrate (e.g., a swab, a sponge, etc.), a non-permeable substrate (e.g., tape, etc.), a container (e.g., vial, tube, bag, etc.) configured to receive a sample from the agriculture site or associated crops, and any other suitable sample-reception element. In a specific example, samples can be collected from one or more of: soil, other crop-associated solids, water, other crop-associated liquids, gases, and a crop component (e.g., root, stem, leaf, flower, seed, other plant component, etc.). In relation to soil samples, samples can be extracted in relation to a reference point (e.g., distance from surface, distance from plant, etc.). In relation to plant components, samples can be taken from a reference (e.g., distance from leaf, distance, from node, distance along root, etc.). In variations in which multiple samples are taken, samples can be pooled (e.g., combined) or kept distinct.

In relation to Block S110, samples can be acquired once, or at several time points within a time period or in relation to a process (e.g., process associated with crop handling, fermentation process, process for preparing crops for consumption, etc.). The time period can be on the order of seconds, minutes, hours, days, months, years, decades, or of any other suitable time scale. In one example, samples were taken at four time points from planting to harvest. However, samples can be taken prior to planting and/or post-harvest.

Furthermore, samples can be received from one or more metacommunities, where a metacommunity is defined as a group of communities within the same habitat/region/pool associated with each agriculture site associated with the set of samples, where the group(s) of communities display multiple possible arrangements according to environmental filters, dispersal restrictions, priority effects and the latter established interactions. As such, features, insights, and actions implemented in subsequent steps of the method can be generated or performed at the metacommunity level and/or at local levels of abstraction.

In other examples, however, samples can be acquired in another suitable manner or from other suitable sources.

In relation to Block Silo, some approximation of the whole method 100 can be run with only latitude and longitude information in the absence of samples. With geostatistical models and Markov processes, the sample characteristics can be predicted without physical sampling, and the method 100 can be subsequently run to provide an ecological picture of the unknown soil. All available information can be modeled while missing information can be imputed implicitly with Bayesian models.

In relation to Block S120, processing the set of samples can include wet lab processing techniques (e.g., sample lysis, sample enrichment, sample purification, target material capture or separation, target amplification, etc.), as well as sequencing and library preparation operations. As such, generating sample data in step S120 includes a combination of sample processing techniques (e.g., wet laboratory techniques) and computational techniques (e.g., utilizing tools of bioinformatics) to quantitatively and/or qualitatively characterize the microbiome, functional features, and/or other aspects (e.g., chemistry) of each sample of the agricultural site(s). Sample processing operations can include generation of one or more of: a full metagenomic dataset, a metatranscriptomics dataset, and a proteomics dataset.

As such, in variations, Block S120 can include one or more of: sample pre-processing (e.g., with homogenization or chopping, with use of a buffer, with formation of a pellet, etc.), sample storage (e.g., at appropriate conditions prior to subsequent processing, e.g., at −80 C, at 4 C, at another suitable temperature, etc.); sample lysis (e.g., using physical methods, using chemical methods, using biological methods, etc.); genetic material (e.g., nucleic acid material) extraction including extraction of DNA, RNA, nucleic acid fragments, or other nucleic acid material; protein extraction; nucleic acid purification (e.g., using precipitation, using liquid-liquid based purification, using chromatography, using binding moiety functionalized particles, etc.); target material capture; removal of sample waste; target incubation; target amplification (e.g., using polymerase chain reaction (PCR)-based techniques, using helicase-dependent amplification (HDA), using loop mediated isothermal amplification (LAMP), using self-sustained sequence replication (3SR), using nucleic acid sequence based amplification (NASBA), using strand displacement amplification (SDA), using rolling circle amplification (RCA), ligase chain reaction (LCR), etc.); target enrichment; and/or any other suitable sample processing steps.

In relation to amplification of nucleic acids, primers used can be designed to mitigate amplification bias effects, as well as configured to amplify nucleic acid regions/sequences (e.g., of the 16S region, 18S region, the ITS region, etc.) that are informative taxonomically, phylogenetically, in relation to emergent properties, for formulations, and/or for any other suitable purpose. Primers used in variations of Block S120 can additionally or alternatively include incorporated barcode sequences, unique molecule identifiers, adaptor sequences, or other sequences specific to each sample and/or in association with sequencing platforms, which can facilitate identification of material derived from individual samples post-amplification. Examples of custom primers are described in WO 2017/096385 published 8 Jun. 2017, which is herein incorporated in its entirety by this reference.

Furthermore, sequencing can be performed in coordination with a next generation sequencing platform (e.g., Illumina™ sequencing platform) or other suitable sequencing platform (e.g., nanopore sequencing platform, PacBio platform, MinION platform, etc.). Additionally or alternatively, any other suitable sequencing platform or method can be used (e.g., a Roche 454 Life Sciences platform, a Life Technologies SOLiD platform, etc.). Additionally or alternatively, sample processing can implement any other step configured to facilitate processing (e.g., using a Nextera kit) for performance of a fragmentation operation (e.g., fragmentation and tagging with sequencing adaptors) in cooperation with amplification. Additionally or alternatively, filtering of sequences (e.g., chimeric sequences, other sequences, etc.) can be performed in coordination with Block S120.

In relation to sample acquisition and sequencing, sample data can be tagged with contextual data, in order to couple identified sample features with various conditions (e.g., perturbations, products, environmental conditions, etc.) in downstream steps of the method. In variations, contextual data can include one or more of: geographic location (e.g., latitude, longitude, altitude); meteorological metadata (e.g., from Dark Sky API); climatic information (e.g., precipitation intensity, precipitation probability, maximum temperature, minimum temperature, dew point, humidity, environmental pressure, wind speed, wind bearing, wind gust, cloud cover, UV index, etc.); environmental disaster information (e.g., fires, hurricanes, tornadoes, earthquakes, temperature variations, etc.); organic management practices (e.g., integrating cultural, biological, and mechanical practices that foster cycling of resources, promote ecological balance, and conserve biodiversity without use of synthetic fertilizers, sewage, irradiation, and genetic engineering); non-organic management practices; use of synthetic fertilizers; use of natural fertilizers; biodynamic management practices (e.g., with generation of their own fertility through composting, integrating animals, cover cropping, and crop rotation); conventional management practices (e.g., with standard farming systems, using a variety of synthetic chemical fertilizers, pesticides, herbicides and other continual inputs, etc.).

In variations, perturbations associated with the agriculture site(s) and/or crops from which samples are derived can include one or more of: a management practice (e.g., a conventional management practice, an organic management practice, and a biodynamic management practice); a regenerative practice (e.g., application of one or more of a cover crop, silvopasture, managed grazing, intercropping, etc.); a biological input including one or more of: a biostimulant, a biofertilizer, a biocontrol agent, a biopesticide, compost, and a biodynamic preparation (wherein the biological input is applied by one or more of: a broadcast spray, an in-furrow spray, seed treatment, application to soil with incorporation, and application to soil without incorporation, etc.); a natural ecological disturbance; and another suitable perturbation.

Data can additionally or alternatively be tagged with metacommunity descriptors, thereby tagging sequence data of the sample dataset with a set of metacommunity descriptors corresponding to a set of communities within a same habitat associated with the agriculture site. In particular, a metacommunity is defined as a group of communities within the same habitat/region/pool associated with each agriculture site associated with the set of samples, where the group(s) of communities display multiple possible arrangements according to environmental filters, dispersal restrictions, priority effects and the latter established interactions. As such, in subsequent steps of the method 100, computing architecture for merging the metacommunity-inferred associations into each of the local communities associated with the set of samples, enables returning of estimations of network properties in all the local communities within the metacommunity, individually, obtaining sample(site)-specific information on microbial ecosystem functioning. Such processes also enable direct comparison among network properties of individual samples, even in the absence of common taxa among them, as all samples are mapped back to the metacommunity, thereby providing a normalization step. Thus, these emergent properties can be implemented as machine-determined universal biomarkers of ecological disturbance.

In relation to model architecture associated with training and refinement of machine learning models described further below, the method described in relation to Block S120 can be used to create training sets of data, in coordination with Block S130 below. As such, training data covering specific sample features and corresponding contextual information related to management practices and other perturbations (e.g., use of various products, environmental perturbations, other agricultural inputs, other practices, etc.) can be used to refine models for predicting effects of various practices and perturbations, and to guide future management practices in a sustainable manner.

In order to process such data, computing platforms implementing one or more portions of the method can be implemented in one or more computing systems, wherein the computing system(s) can be implemented at least in part in the cloud and/or as a machine (e.g., computing machine, server, mobile computing device, etc.) configured to receive a computer-readable medium storing computer-readable instructions. However, Block S120 can be performed using any other suitable system(s).

Sample processing and generating of a sample dataset can be performed according to embodiments, variations, and examples of method steps described in U.S. application Ser. No. 17/119,972 filed on 11 Dec. 2020 and U.S. application Ser. No. 17/587,016 filed on 28 Jan. 2022, incorporated by reference above.

2.2 Methods—Generating Microbiome-Associated Features, with Taxonomic Annotations, Functional Annotations, and Ecological Indices Block S130 recites: generating a set of microbiome-associated features, including taxonomic annotations, functional annotations, and/or ecological indices for characterization of the set of agricultural samples, upon performing a set of transformation operations upon the sample dataset. Block S130 functions to generate ecological indices and/or other microbiome-associated features, which can be used for analyses of crops, agricultural site characteristics, and/or other analyses for improving outcomes.

In variations, Block S130 can include generation of taxonomic annotations related to operational taxonomic units (OTUs), amplicon sequence variants (ASVs), diversity metrics (e.g., alpha-diversity metrics, beta-diversity metrics, gamma-diversity metrics, etc.), and/or quantifications of various taxonomic units (e.g., relative quantifications, absolute quantifications).

In variations, Block S130 can include generation of functional annotations related to characterization of nutrient metabolic pathways, species or other organisms that function as plant growth promoters (PGPs, phytohormone producing species, stress tolerance molecule-producing species, etc.), species or other organisms that provide biocontrol functions, organisms that produce disease resistance functions, functional diversity, and/or other suitable functional annotations.

In variations, Block S130 can include generation of ecological indices related to characterization of resilience (e.g., based upon transitivity of bacterial networks and/or fungal networks), disease risk (e.g., crop-specific disease risks based upon abundances of pathogens and soil microbiome resilience), health (e.g., based upon summary of health and disease risks), sustainable productivity (e.g. trained on known traditional, organic and biodynamic soil samples), combinations of taxonomic indices and functional indices with network properties, and/or other suitable ecological indices.

The invention(s) can additionally or alternatively include aspects described in U.S. application Ser. No. 17/119,972 filed on 11 Dec. 2020 and U.S. application Ser. No. 17/587, 016 filed on 22 Jan. 2022, incorporated by reference above.

2.2.1 Taxonomic—Operational Taxonomic Unit (OTU) and Amplicon Sequence Variant (ASV) Processes Variations of Block S130 can include generation of OTU-associated features and/or ASV-associated features for taxonomy annotation.

In relation to OTU-associated features and ASV-associated features, samples can be processed as described in U.S. App. No. 17/119,972 filed on 11 Dec. 2020 (incorporated by reference above) and/or related applications. In particular, processing steps can include sample storage, DNA extraction, amplification (e.g., by a PCR protocol), sequencing (e.g., paired-end sequencing), library preparation (e.g., in relation to 16S rRNA V4 regions, in relation to ITS1 regions, etc.) using custom primers as described above, sequence analysis (e.g., using VSEARCH), and/or other suitable process steps.

In an example, raw paired-end FASTQ sequences (forward and reverse paired reads) were merged, filtered by an expected error 0.25, dereplicated, and sorted by size. Chimera sequences were filtered out in coordination with clustering of non-singleton sequences into 97% identity operational taxonomic units (OTUs) (e.g., a mapping of sequences output by the filtering operation to operational taxonomic units (OTUs) with an identity threshold), or into amplicon sequence variants (ASVs) using a single mismatch (99.7% identity). For OTU-associated features, taxonomic annotation was performed (e.g, using a SINTAX algorithm, using algorithms that implement k-mer similarity metrics to identify top taxonomic candidates for annotation, using algorithms that identify full-length alignments to reference sequences, etc.). In one example, all combined sequences were then mapped to a list of 31, 516 OTUs with at least 97% identity, resulting in an OTU table with 54,738, 544 sequences, averaging 156,395 sequences per soil sample. The OTU richness of samples averaged 529 OTUs (e.g., in relation to a range of 23-4999 OTUs) per soil sample. OTUs were then classified (e.g., with a UNITE database according to a UTAX pipeline, with a SILVA 123 database through a SILVA-NGS pipeline). However, variations of the example can implement other sequencing protocols, OTU mapping, OTU classification algorithms, and/or other methods.

In variations, the method can additionally or alternatively include processing and assessment of amplicon sequence variants (ASVs). In particular, during sequencing, it is expected that some nucleotide sequences may be subject to sequencing errors; thus, examples of the methods can include clustering of reads to compensate for sequencing errors. In particular, grouping similar sequences to form clusters which are represented by the centroid sequence (i.e., the most abundant sequence of the cluster) can be implemented. In situations where a 97% sequence identity threshold for OTUs is too inclusive for some species, processes of the method can include clusterization between sequences with a difference of only one nucleotide, in order to maintain the highest possible granularity and keep small differences visible, such that they can be annotated separately. Thus, in certain variations, ASV-associated approaches can significantly increase the number of final sequences to annotate for the same sample, increasing resolution and allowing better discrimination of closely related species. The method can thus include performance of annotation of ASVs against curated taxonomic databases based on exact sequence matches, with assessment of in silico performance metrics for the annotation of each ASV. In specific applications, ASVs from 16S regions provided suitable performance metrics (e.g., >90% sensitivity, >90% specificity, >90% positive predictive value, >90% negative predictive value, etc.) for identifying ~46% of the species and ~8 9% of the genera. ASVs from ITS regions also provided good performance metrics for identifying ~8 7% of species and ~97% of the genera.

In variations, Bayes factors derived from the posterior odds of a connection between OTUs or ASVs can be used as edge-weights for weighted directed networks, and derivative features processed by models associated with the methods.

2.2.2 Taxonomic—Taxonomic Quantification

In more detail with respect to quantification of sample organisms (e.g., prokaryotes and fungi), variations of Block S130 can include processing a combination of multiple microorganism strains that are added in known amounts to a sample, and running the sample in replication through next generation sequencing (NGS). In examples, two bacterial strains (e.g., a Gram + and a Gram − strain) can be processed, and each sample can be run in replicate (e.g., one replicate, two replicates, three replicates, four replicates, etc.) for quantification (e.g., absolute quantification of sample microorganisms).

The invention(s) then include extrapolation of a number of 16S copies from the microorganism strains added in known concentrations in relation to the rest of the microorganisms in the sample, and then correcting by 16S copy number to obtain the final absolute concentration of each organism (e.g., bacterial organism, archaeal organism) present.

In variations, the invention(s) can additionally or alternatively implement a synthetic construct having an example format:

[16S FW Primer][its FW Primer][Random SEQ Based on 16S and ITS][16S RV Complement Primer][its RV Complement Primer].

In examples, the [RANDOM SEQ BASED ON 16S AND ITS] can have desired aspects. In one such example, the random sequence is composed of a portion (e.g., first half) of a 16S amplicon from a first organism (e.g., *Rhizobium pusense*) and a portion (e.g., first half) of an ITS amplicon from a second organism (e.g., *Solicoccozyma phenolica*), after which the nucleotide order was shuffled randomly. In this example, the [RANDOM SEQ BASED ON 16S AND ITS] has the a desired sequence; however, in other examples, the random sequence can be generated in another suitable manner (e.g., based upon shuffling of sequence portions from other amplicons of other organisms).

In the example above, the random sequence has a 46% GC and is not similar to any sequence in the NT database, so is unique enough to be distinguished from extant bacteria and fungi. The invention(s) also include steps for evaluating and detecting potential secondary structures of the synthetic construct to ensure it is in a similar energy range to that of an ITS amplicon, or that of a 16S amplicon. However, the random sequence can have another suitable format.

In relation to quantification, Block S130 can include addition of synthetic spike to samples in known concentration, in order to perform absolute quantification of sample organisms (e.g., prokaryotes and fungi) simultaneously. In variations, the synthetic spike (e.g., of exogenous bacteria with known microbial composition into samples) can be run in replication (e.g., one sample with no replication, two replicates, three replicates, etc,). Furthermore, in other variations, the synthetic spike can be used to quantify several sample types (e.g., soils, soil amendments, tissue samples, produce samples, etc.).

Taxonomic annotation data in relation to quantification can be presented at any taxonomic level (i.e. phylum, class, order, family, genus, species, subspecies).

Additionally or alternatively, taxonomic annotation can be presented in relation to ratios between different types of organisms (e.g., a bacterial:fungal ratio, an endomycorrhizae:ectomycorrhizae ratio, or any other suitable ratio).

In examples, shown in FIGS. 2A-2F, taxonomic features can include descriptions of detected populations (e.g. microbial population distributions, fungal population distributions), with breakdowns of compositions (e.g., in percentages) for different taxonomic groups/ranks. Exemplary representative bacterial phylum distributions (e.g., Firmicutes, proteobacteria, bacteroidetes, planctomycetes, actinobacteria, etc.) and representative fungal phylum distributions (e.g., ascomycota, basidiomycota, zygomycota, glomeromycota, etc.) are depicted in FIGS. 2A-2F, with additional features associated with quantification of specific species (e.g., *Bacillus lichenformis, Clostridium isotidis, Bacillus subtilis, Escherichia coli, Bacillus amyloliquefaciens, Bacillus megaterium*, etc.). However, variations of the example features can be returned by outputs of Block S130.

2.2.3 Taxonomic—Diversity Metrics

In more detail with respect to generation of diversity features with respect to taxonomic annotation, variations of Block S130 can include steps for performing alpha-, beta-, and/or gamma-diversity analyses in relation to various taxonomic groups and/or associated features. For instance, variations of the method include steps for performing alpha- and beta diversity analyses using 16S and ITS ASV or OTU counts (e.g., using R vegan), where alpha-diversity metrics (e.g., Shannon, richness, etc.) were calculated and plotted across all covariates available. In relation to various inputs and/or practices, Block S130 can implement architecture for performing tests (e.g., Wilcoxon rank-sum tests) to compare samples associated with different inputs and/or management practices (e.g., control and treatment groups) within various subgroups.

In variations of Block 130, alpha-diversity analyses can include rarefaction of samples to a common desired sequencing depth (e.g., 20,000 reads, 10,000 reads, etc.) and replicating the rarefaction a number of times to ensure the results of the subsample are representative of the entire sample (e.g., repeating 10 times, repeating 50 times, repeating 100 times, repeating 500 times, etc.)

For beta-diversity, the Block S130 can implement architecture for determining beta-diversity characteristics. For instance, in one variation, Block S130 includes steps for implementing Kruskal's non-metric multidimensional scaling in conjunction with Aitchison distances. Block S130 can also implement architecture for performing permutational multivariate analysis of variance on the Aitchison distance matrix, using all possible combinations of the location, timepoint and treatment variables.

However, other variations of methods for characterizing diversity metrics and/or other statistical methods can be implemented.

2.2.4 Taxonomic—Abundance

Block S130 can also implement architecture for determining abundance parameters (e.g., relative abundances) in relation to various groups of organisms, for various analyses. For instance, in one such variation, relative/absolute abundance parameters determined from outputs of Block S130 can be used for determination of crop-specific disease risk or other insights, in relation to variations of Blocks S140 and S150 described in more detail below.

In some variations, Block S130 can thus apply sample processing techniques and data processing steps associated with determining relative and absolute abundance of various groups (e.g., groups of kingdoms, phyla, classes, orders, families, genera, species, subspecies, strains, infraspecies taxa, etc.) represented in samples from the agricultural site(s), with direct measurements and/or functional inference based on the taxonomic abundances and/or ecological network factors.

In a specific example related to abundance-associated features, Block S130 can include implementation of methods for determining differential abundance of various OTUs/ASVs. In more detail, in a specific example, zero counts in data were replaced, where valid values for replacement were calculated under a Bayesian paradigm, assuming a Dirichlet prior. Non-zero values were then adjusted to maintain the overall composition using a pairwise comparison process for differential expression analysis (e.g., edgeR algorithm), thereby determining differential abundance of various groups represented in a sample.

Outputs of Block S130 can then be used for responding to an issue detected at the agriculture site(s) being assessed (e.g., in relation to pathogen presence or increased abundance of a detrimental microorganism, in relation to decreased abundance of a beneficial microorganism, in relation to correcting a perturbation, in relation to adjusting application of a product at the agriculture site, implementing protective measures against environmental effects, etc.); responding to or otherwise correcting other undesired statuses at one or more agriculture sites being monitored; providing information regarding site characteristics to a manager/operator/other entity associated with the agriculture site(s); performing decision-making guidance (e.g., in relation to analyses indicative of sustainability of practices, in relation to long term effects of use of one or more products, etc.); and performing other suitable actions, described in more detail below.

The method can, however, include other method steps and/or process outputs based upon abundance measurements in another suitable manner.

In examples, relative abundance features can include relative abundances of taxonomic groups (e.g., genus and species, other taxonomic groups), where exemplary fungal groups shown include: *Trichoderma atroviride, Wallemia mellicola, Penicillium dierckxii, Naganishia diffluens, Penicillium rubens, Alternaria alternata, Epicoccum nigrum, Talaromyces marneffei, Penicillium citrinum, Coniothyrium* sp. *Xenomyrothecium tongaense, Resinicium rimulosum, Meyerozyma guilliermondii, Candida tropicalis, Wallemia hederae, Chaetomium globosum, Aspergillus fumigatus, Ganoderma applanatum, Coprinopsis gonophylla, Aspergillus terreus, Wallemia sebi, Cladosprium herbarum, Alternaria metachromatica, Fusarium oxysproum, Nigrospora oryzae, Arachnomyces pilosus, Penicillium pimiteouiense, Wallemia* sp., *Aspergillus pseudoglaucus, Ovatospora medusarum, Lophotrichus fimeti, Rhizophagus irregularis, Neofavolus alveolaris, Penicillium melinii, Penicillium herquei, Trichosporon asahii, Aspergillus versicolor, Penicillium erubescens, Humicola olivacea, Penicillium cinnamopurpureum, Schizothecium inoequale, Rhizopus oryzae, Penicillium parvulum, Penicillium brevicocompactum,*

*Penicillium restrictum*, *Zopfiella erostrata*, *Collariella bostrychodes*, *Aspergillus* sp, *Mycosphaerella coffeicola*, *Penicillium polonium*, etc. However, variations of the example features can be returned by outputs of Block S130.

Furthermore, outputs of Block S130 can further implement steps for functional annotation and/or generation of ecological indices as described in related applications and below, which can be processed individually and/or in combination with taxonomic annotation in relation to generation of agronomic indices in Block S140 below.

2.2.5 Functional—Nutrient Metabolic Pathways

In more detail with respect to generation of features related to nutrient metabolic pathways, Block S130 can include steps for predicting metagenomic composition of a sample based on sequences (e.g., amplicon sequences, sequences associated with operational taxonomic units, etc.) processed according to embodiments, variations, and examples of Block S120 above. In variations, however, full metagenomic sequences can be obtained for the samples, at appropriate sequencing depth, so enzyme sequences can be directly annotated from raw sequencing data as opposed to being predicted based on amplicon sequencing. Data associated with metagenomic composition can then be processed further and transformed to extract features related to nutrient metabolic pathways, with respect to effects of sample microbiota upon soil macronutrients and micronutrients.

In one variation, Block S130 can include generating a predicted metagenomic functional factors/composition of one or more samples acquired from the agricultural site(s), wherein generating the predicted metagenomic composition comprises extracting functional annotations associated with the sequences from a suitable database (e.g., a custom database, the Kyoto Encyclopedia of Genes and Genomes (KEGG) database, etc.). Block S130 can then include architecture for identifying specific enzymes from the metagenomes, in relation to those specific enzymes most informative for each type of nutrient metabolic cycle in soil. As such, outputs of Block S130 can include features associated with enzymes corresponding to each nutrient metabolic pathway, with scores at pathway-level (e.g., aggregate) and nutrient-level scales.

In examples, outputs of Block S130 can include features associated with carbon pathways (e.g., carbon fixation, aerobic respiration, fermentation, methanogenesis, organic matter release, in terms of percentages, in terms of gain and loss, in terms of supply, in terms of competition, in terms of indirect benefits, etc.) with respect to specific enzyme annotations derived from suitable databases. In examples, enzymes associated with carbon pathways can include one or more of: ribulose-bisphosphate carboxylase large or small chain [EC:4.1.1.39], cytochrome c oxidase subunit I [EC: 1.9.3.1], 2-oxoglutarate/2-oxoacid ferredoxin oxidoreductase subunit alpha [EC:1.2.7.3 1.2.7.11], fumarate reductase flavoprotein subunit [EC:1.3.5.4], methane monooxygenase component A alpha or beta chain [EC: 1.14.13.25], aerobic carbon-monoxide dehydrogenase small or large subunit [EC:1.2.5.3], L-lactate dehydrogenase [EC: 1.1.1.27], methyl coenzyme M reductase system, component A2, methyl-coenzyme M reductase beta subunit [EC: 2.8.4.1], acetyl-CoA decarbonylase/synthase complex subunit [EC:2.1.1.245], endoglucanase [EC:3.2.1.4], endo-1,3 (4)-beta-glucanase [EC:3.2.1.6], beta-glucuronidase [EC: 3.2.1.31], cellulose 1,4-beta-cellobiosidase [EC:3.2.1.91], beta-glucosidase [EC:3.2.1.21], cellobiose epimerase [EC: 5.1.3.11], chitinase [EC:3.2.1.14], chitin deacetylase [EC: 3.5.1.41], putative chitinase, chitin-binding protein, bifunctional chitinase/lysozyme [EC:3.2.1.14 3.2.1.17], endo-1,4-beta-xylanase [EC:3.2.1.8], xylan 1,4-beta-xylosidase [EC: 3.2.1.37], mannan endo-1,4-beta-mannosidase [EC: 3.2.1.78], arabinogalactan endo-1,4-beta-galactosidase [EC: 3.2.1.89], galactonate dehydratase [EC:4.2.1.6], alpha-D-xyloside xylohydrolase [EC:3.2.1.177], oligosaccharide reducing-end xylanase [EC:3.2.1.156], arabinoxylan arabinofuranohydrolase [EC:3.2.1.55], glucuronoarabinoxylan endo-1,4-beta-xylanase [EC:3.2.1.136], catechol 2,3-dioxygenase [EC:1.13.11.2], biphenyl 2,3-dioxygenase subunit alpha [EC:1.14.12.18], naphthalene 1,2-dioxygenase subunits [EC:1.14.12.12 1.14.12.23 1.14.12.24], cis-1,2-dihydro-1,2-dihydroxynaphthalene/dibenzothiophene dihydrodiol dehydrogenase [EC:1.3.1.29 1.3.1.60], biphenyl 2,3-dioxygenase subunit beta [EC:1.14.12.18], or other suitable enzymes.

In examples, outputs of Block S130 can include features associated with nitrogen pathways (e.g., inorganic nitrogen cycle health, inorganic nitrogen consumption, inorganic nitrogen release, in terms of percentages, in terms of gain and loss, in terms of supply, in terms of competition, in terms of indirect benefits, etc.) with respect to specific enzyme annotations derived from suitable databases. In examples, enzymes associated with nitrogen pathways can include one or more of: nitrite reductase (cytochrome c-552) [EC: 1.7.2.2], hydroxylamine dehydrogenase [EC:1.7.2.6], nitrite reductase (NO-forming) [EC:1.7.2.1], nitrous-oxide reductase [EC:1.7.2.4], nitric oxide reductase subunit C, nitric oxide reductase subunit B [EC:1.7.2.5], nitrite reductase (NO-forming)/hydroxylamine reductase [EC: 1.7.2.1 1.7.99.1], glutamate synthase (NADPH/NADH) large chain [EC:1.4.1.13 1.4.1.14], glutamate synthase (ferredoxin) [EC:1.4.7.1], assimilatory nitrate reductase electron transfer subunit [EC:1.7.99.-], ferredoxin-nitrate reductase [EC:1.7.7.2], nitrogenase delta subunit [EC: 1.18.6.1], glutamine synthetase [EC:6.3.1.2], nitrogenase molybdenum-iron protein alpha chain [EC:1.18.6.1], nitrogenase iron protein NifH [EC:1.18.6.1], nitrogenase molybdenum-iron protein beta chain [EC:1.18.6.1], glutamate dehydrogenase [EC:1.4.1.2], glutamate dehydrogenase (NAD(P)+) [EC:1.4.1.3], periplasmic nitrate reductase NapA [EC:1.7.99.-], cytochrome c-type protein NapB, nitrate reductase/nitrite oxidoreductase, alpha subunit [EC: 1.7.5.1 1.7.99.-], nitrate reductase/nitrite oxidoreductase, beta subunit [EC:1.7.5.1 1.7.99.-], methane/ammonia monooxygenase subunits [EC:1.14.18.3 1.14.99.39], or other suitable enzymes.

In examples, outputs of Block S130 can include features associated with phosphorus pathways (e.g., inorganic phosphorus assimilation, organic phosphorus assimilation, phosphorus solubilization, phosphorus consumption in terms of percentages, in terms of gain and loss, in terms of supply, in terms of competition, in terms of indirect benefits, etc.) with respect to specific enzyme annotations derived from suitable databases. In examples, enzymes associated with phosphorus pathways can include one or more of: phosphate transport system ATP-binding protein [EC:3.6.3.27], phosphate transport system permease protein, low-affinity inorganic phosphate transporter, GntR family transcriptional regulator, phosphonate transport system regulatory protein, 2-aminoethylphosphonate-pyruvate transaminase [EC:2.6.1.37], phosphonoacetaldehyde hydrolase [EC:3.11.1.1], ribose 1,5-bisphosphokinase [EC:2.7.4.23], alpha-D-ribose 1-methylphosphonate 5-triphosphate synthase subunit PhnL [EC:2.7.8.37], putative phosphonate transport system ATP-binding protein, alpha-D-ribose 1-methylphosphonate 5-triphosphate diphosphatase [EC:3.6.1.63], alpha-D-ribose 1-methylphosphonate 5-phosphate C-P lyase [EC:4.7.1.1], alpha-D-ribose 1-methylphosphonate 5-triphosphate synthase subunits [EC:2.7.8.37], phosphonate transport system ATP-binding protein [EC:3.6.3.28], phosphonate transport system permease protein, phosphonate transport system substrate-binding protein, PhnB protein, protein PhnA, pyrroloquinoline-quinone synthase [EC:1.3.3.11], or other suitable enzymes.

In examples, outputs of Block S130 can include features associated with potassium pathways (e.g., potassium consumption, potassium solubilization, in terms of percentages, in terms of gain and loss, in terms of supply, in terms of competition, in terms of indirect benefits, etc.) with respect to specific enzyme annotations derived from suitable databases. In examples, enzymes associated with potassium pathways can include one or more of: trk system potassium uptake protein, two-component system, OmpR family, sensor histidine kinase KdpD [EC:2.7.13.3], two-component system, OmpR family, KDP operon response regulator KdpE, KUP system potassium uptake protein, pyrroloquinoline-quinone synthase [EC:1.3.3.11], or other suitable enzymes.

In examples, outputs of Block S130 can include features associated with iron pathways (e.g., iron assimilation, etc.) with respect to specific enzyme annotations derived from suitable databases. In examples, enzymes associated with iron pathways can include one or more of: enterobactin synthetase component D [EC:6.3.2.14 2.7.8.-], enterobactin synthetase component F [EC:6.3.2.14], MFS transporter, ENTS family, enterobactin (siderophore) exporter, ATP-binding cassette, subfamily B, salmochelin/enterobactin exporter, ferric enterobactin receptor, outer membrane receptor for ferrienterochelin and colicins, ferrous iron transport proteins, or other suitable enzymes.

In examples, outputs of Block S130 can include features associated with zinc pathways (e.g., zinc transport equilibrium, etc.) with respect to specific enzyme annotations derived from suitable databases. In examples, enzymes associated with zinc pathways can include one or more of: cobalt-zinc-cadmium efflux system protein, zinc transport system substrate-binding protein, zinc transport system permease protein, zinc transport system ATP-binding protein [EC:3.6.3.-], or other suitable enzymes In examples, outputs of Block S130 can include features associated with manganese pathways (e.g., manganese transport equilibrium, in terms of percentages, in terms of gain and loss, in terms of supply, in terms of competition, in terms of indirect benefits, etc.) with respect to specific enzyme annotations derived from suitable databases. In examples, enzymes associated with phosphorus pathways can include one or more of: manganese/zinc transport system substrate-binding protein, manganese/zinc transport system permease protein, manganese/zinc transport system ATP-binding protein [EC:3.6.3.35], manganese transport protein, manganese transport system substrate-binding protein, or other suitable enzymes.

In examples, outputs of Block S130 can include features associated with sulfur pathways (e.g., sulfur cycle equilibrium, in terms of percentages, in terms of gain and loss, in terms of supply, in terms of competition, in terms of indirect benefits, etc.) with respect to specific enzyme annotations derived from suitable databases. In examples, enzymes associated with sulfur pathways can include one or more of: adenylylsulfate kinase [EC:2.7.1.25], sulfate adenylyltransferase subunit 1 [EC:2.7.7.4], sulfate adenylyltransferase subunit 2 [EC:2.7.7.4], thiosulfate reductase/polysulfide reductase chain A [EC:1.8.5.5], cysteine dioxygenase [EC:1.13.11.20], thiosulfate/3-mercaptopyruvate sulfurtransferase [EC:2.8.1.1 2.8.1.2], adenylylsulfate reductase, subunits [EC:1.8.99.2], dissimilatory sulfite reductase alpha subunit [EC:1.8.99.5], sulfur-oxidizing proteins, or other suitable enzymes.

In examples, outputs of Block S130 can include features associated with calcium pathways (e.g., calcium transport, etc.) with respect to specific enzyme annotations derived from suitable databases. In examples, enzymes associated with calcium pathways can include one or more of: Ca2+:H+ antiporter, cation:H+ antiporter, or other suitable enzymes.

In examples, outputs of Block S130 can include features associated with copper pathways (e.g., copper export, in terms of percentages, in terms of gain and loss, in terms of supply, in terms of competition, in terms of indirect benefits, etc.) with respect to specific enzyme annotations derived from suitable databases. In examples, enzymes associated with copper pathways can include one or more of: Cu+-exporting ATPase [EC:3.6.3.54], outer membrane protein, Cu(I)/Ag(I) efflux system, or other suitable enzymes.

In examples, outputs of Block S130 can include features associated with chlorine pathways (e.g., chlorine transport, in terms of percentages, in terms of gain and loss, in terms of supply, in terms of competition, in terms of indirect benefits, etc.) with respect to specific enzyme annotations derived from suitable databases. In examples, enzymes associated with chlorine pathways can include one or more of: chloride channel CLIC-like protein 1, solute carrier family 12 (sodium/potassium/chloride transporter) members, chloride channel protein, CIC family, Ca-activated chloride channel homolog, or other suitable enzymes.

In examples, outputs of Block S130 can include features associated with magnesium pathways (e.g., magnesium transport, in terms of percentages, in terms of gain and loss, in terms of supply, in terms of competition, in terms of indirect benefits, etc.) with respect to specific enzyme annotations derived from suitable databases. In examples, enzymes associated with magnesium pathways can include one or more of: Mg2+-importing ATPase [EC:3.6.3.2], magnesium transporter, putative Mg2+ transporter-C (MgtC) family protein, phosphatidylinositol alpha 1,6-mannosyltransferase [EC:2.4.1.-], magnesium transporter, or other suitable enzymes.

Output features of Block S130 can, however, include other features associated with other micronutrient and/or macronutrient metabolic pathways, some examples of which are described in applications incorporated by reference.

2.2.6 Functional—Plant Growth Promotors (PGPs)

In more detail with respect to generation of features related to plant growth promotors (PGPs), Block S130 can include steps for directly mapping the genera and/or species that result from other annotations (e.g., taxonomic annotations described in related applications and/or applications incorporated by reference) to curated databases of microorganisms. Block S130 can, however, implement other mapping or transformation algorithms for generating features associated with PGPs.

In examples, outputs of Block S130 can include features with respect to specific organism annotations (e.g., in a crop-agnostic manner, in a crop-specific manner) derived from suitable databases, where the features are associated with one or more of: salt tolerance, heavy metal solubilization, indoleacetic acid production, cytokinin production, gibberellin production, ACC deaminase, exopolysaccharide production, abscisic acid, salicylic acid, siderophore production, or other suitable plant growth promotor features.

Output features of Block S130 can, however, include other features associated with other plant growth promotor features, some examples of which are described in applications incorporated by reference.

2.2.7 Functional—Biocontrol Species

In more detail with respect to generation of features related to biocontrol species, Block S130 can include steps for directly mapping the genera and/or species that result from other annotations (e.g., taxonomic annotations described in related applications and/or applications incorporated by reference) to curated databases of microorganisms. Block S130 can, however, implement other mapping or transformation algorithms for generating features associated with biocontrol species.

In examples, outputs of Block S130 can include features with respect to specific organism annotations (e.g., in a crop-agnostic manner, in a crop-specific manner) derived from suitable databases, where the features are associated with one or more of: fungicide biocontrol agents, bactericide biocontrol agents, nematicide biocontrol agents, insecticide biocontrol agents, or other suitable biocontrol agent features (e.g., in terms of abundances represented). Such agents can thus be grouped according to the types of "pests" they encounter and/or capabilities for preventing pathogenic taxonomic groups from proliferating.

Output features of Block S130 can, however, include other features associated with other biocontrol species features, some examples of which are described in applications incorporated by reference.

2.2.8 Functional—Overall Functional Diversity Metrics

In more detail with respect to generation of diversity features with respect to functional annotation, variations of Block S130 can include steps for performing alpha-, beta-, and/or gamma-diversity analyses in relation to various features. For instance, variations of the method include steps for performing alpha- and beta diversity analyses (e.g., derived from 16S and ITS ASV or OTU counts associated with taxonomies and/or functional features), where alpha-diversity metrics (e.g., Shannon, richness, etc.) were calculated and plotted across all covariates available. In relation to various inputs and/or practices, Block S130 can implement architecture for performing tests (e.g., Wilcoxon rank-sum tests) to compare samples associated with different inputs and/or management practices (e.g., control and treatment groups) within various subgroups.

In variations of Block 130, functional diversity analyses can include rarefaction of samples to a common desired sequencing depth (e.g., 100,000 reads, 50,000 reads, 20,000 reads, 10,000 reads, etc.) and replicating the rarefaction a number of times to ensure the results of the subsample are representative of the entire sample (e.g., repeating 10 times, repeating 50 times, repeating 100 times, repeating 500 times, etc.)

For beta-diversity, the Block S130 can implement architecture for determining beta-diversity characteristics. For instance, in one variation, Block S130 includes steps for implementing Kruskal's non-metric multidimensional scaling in conjunction with Aitchison distances. Block S130 can also implement architecture for performing permutational multivariate analysis of variance on the Aitchison distance matrix, using all possible combinations of the location, timepoint and treatment variables.

However, other variations of methods for characterizing diversity metrics and/or other statistical methods can be implemented.

Furthermore, outputs of Block S130 can further implement steps for taxonomic annotation and/or generation of ecological indices as described in related applications, which can be processed individually and/or in combination with functional annotation in relation to generation of agronomic indices in Block S140 below.

2.2.9 Ecological—Resilience Indices

In more detail with respect to generation of features related to resilience, Block S130 can include steps for generating values of resilience indices based upon or otherwise derived from transitivity of bacterial networks and fungal networks. In variations, resilience indices can be determined based upon processing features associated with co-inclusion and co-exclusion factors generated from sample processing and analysis operations described above and/or in U.S. App. No. 1 7/119,972 filed 11 Dec. 2020.

In particular, in order to generate resilience indices, Block S130 can include generating a network property dataset (e.g., with respect to bacterial networks, with respect to fungal networks, with respect to other organism networks, etc.) from outputs of Blocks Silo and S120, and then processing the network property dataset with architecture for implementing one or more processes including: transforming a first grouping of positive pairs of organisms and a second grouping of negative pairs of organisms (i.e., organisms represented in the sample dataset, related to co-inclusion and co-exclusion, respectively) into one or more aggregate matrices representing co-inclusion parameters (e.g., the whole number of potential associations between all the taxa in the pool, associations that are described as system relevant interdependencies including: biotic interactions, environmental affinities, dispersal restrictions, etc.) and co-exclusion parameters (e.g., for various taxonomic units associated with metacommunities or other communities represented in the set of samples); subdividing the one or more aggregate matrices into a set of individual matrices containing features associated with only the species (or other taxonomic units) occurring in each of the set of samples; performing co-inclusions and/or co-exclusion estimations in a suitable manner (e.g., based upon covariance determination methods, based upon correlation determination methods, with SparCC, with SPIECeasi etc.); processing the set of individual matrices in order to generate a set of undirected network mappings with nodes representing species (or other taxonomic units) and edges representing statistically significant co-inclusions/co-exclusions; and performing other suitable data processing steps.

Then, in relation to Block S130, the computing platform can implement architecture for extracting features associated with transitivity from the set of undirected network mappings, where features can be derived from extraction of interconnections between adjacent and non-adjacent nodes of the network mappings, as a proxy for the tightness of connected communities. Such transitivity features can then be processed in order to generate values of resilience indices associated with the set of samples.

Additionally or alternatively, resilience indices can be generated from features including one or more of: a number of connected components (i.e., defined in relation to a subnetwork in which any two nodes connect to each other by edges, that lack connection to other nodes in the full network); a modularity factor (e.g., a quality of a partition into modules such as groups of nodes using a quantity of edges inside modules compared to a quantity of edges between modules, using an appropriate clustering algorithm (e.g. walktrap, Louvain, fast greedy, edge-betweenness, etc.); a clustering coefficient; an average path length between network components (i.e., defined as a mean of the minimal number of required edges to connect any two nodes); an assortativity factor (e.g., a feature which measures homophyly of a network, according to node properties or labels such as node degree, which quantifies the number of edges associated to a node); a proportion of co-inclusion factor normalized to a total number of combinations of all OTUs/ASVs in the sample(s); a proportion of co-exclusion factor normalized to a total number of combinations of all OTUs/ASVs in the sample(s); and other suitable features.

Resilience indices can then be used to characterize aspects and effects of any input/management practice for any crop, agriculture site, and/or soil type, where the input/management practice alters the structure of microbial communities of the soil, and a decreased transitivity (and thus, resilience) on the network (e.g., fungal network, bacterial network) can indicate such an effect. Resilience index outputs of Block S130 can, however, be derived in another suitable manner, some examples of which are described in applications incorporated by reference.

2.2.10 Ecological—Disease-Risk Associated Functions

In more detail with respect to generation of features related to disease-risk associated functions, Block S130 can include steps for directly mapping the genera and/or species that result from other annotations (e.g., taxonomic annotations described in related applications and/or applications incorporated by reference) to curated databases of microorganisms, and extracting disease risk-associated features accordingly. Block S130 can, however, implement other mapping or transformation algorithms for generating features associated with disease risk in another suitable manner.

In examples, outputs of Block S130 can include features with respect to specific organism annotations (e.g., in a crop-agnostic manner, in a crop-specific manner) derived from suitable databases, where the features are associated with disease risk as disease-risk indices in relation to one or more of rot, scab, wilt, blight, scurf, canker, wart, dot, spot, pit, blotch, rust, gangrene, mold, leak, mildew, smut, or other suitable diseases. Disease risk-associated features can further be associated with any part of any crop. In examples, disease risk-associated features can be generated in association with one or more of: bacterial rot, charcoal rot, common scab, other scab, early blight, *Fusarium* dry rot, *Fusarium* wilt, late blight, pink eye, pink rot, ring rot, powdery scab, black scurf and stem canker, *Verticillium* wilt, wart, black dot, brown spot, black pit, *Cercospora* leaf blotch, *Choanephora* blight, common rust, deforming rust, gangrene, grey mold, leak, *Phoma* leaf spot, *Pleospora herbarum*, powdery mildew, *Rosellinia* black rot, *Septoria* blight, silver scurf, skin spot, stem rot, *Thecaphora* smut, *Ulocladium* blight, white mold, zebra chip disease, or other suitable disease-associated features.

Exemplary disease-risk associated features for soil potatoes can additionally or alternatively include: bacterial soft rot and black leg (e.g., from tubers, associated with *Pectobacterium atrosepticum, Pectobacterium carotovorum*, etc.); bacterial wilt or brown rot (e.g., from leaves, associated with *Ralstonia solanacearum*, etc.); charcoal rot (e.g., from tubers, associated with *Macrophomina phaseolina*, etc.); common scab (e.g., from tubers, associated with *Streptomyces acidiscabies, Streptomyces scabiei, Streptomyces turgidiscabies*, etc.); early blight (e.g., from leaves, stems, and tubers, associated with *Alternaria solani, Macrophomina phaseolina, Fusarium acuminatum*, etc.); *Fusarium* dry rot (e.g., from tubers, associated with *Fusarium acuminatum, Fusarium avenaceum, Fusarium culmorum, Fusarium equiseti, Fusarium oxysporum, Fusarium solani, Fusarium* sp., etc.); *Fusarium* wilt (e.g., from leaves, associated with *Fusarium avenaceum, Fusarium oxysporum, Fusarium solani, Fusarium* sp., etc.); late blight (e.g., from leaves, stems, tubers, associated with *Botrytis cinerea, Pseudomonas fluorescens, Phytopththora cryptogea*, etc.); pink eye (e.g., associated with *Pseudomona florescens*, etc.); pink rot (e.g., associated with *Phytophthora drechsleri, Phytophthora megasperma, Phytophthora nicotianae, Phytophthora* sp., etc.); ring rot (e.g., associated with *Clavibacter michiganesis*, etc.); powdery scab (e.g., from tubers, associated with *Spongospora subterranea*, etc.); black scurf stem canker (e.g., from tubers, associated with *Rhizoctonia solani*, etc.); verticillium wilt (e.g., from roots, stems, and leaves, associated with *Verticillium albo-atrum, Verticillium dahliae*, etc.); wart (e.g., from tubers, associated with *Synchytrium endobioticum*, etc.); black dot (e.g., from tubers, associated with *Colletotrichum agaves*, etc.); brown spot and black pit (e.g., associated with *Alternaria alternata*, etc.); *Cercospora* leaf blotch (e.g., associated with *Cercospora solani*, etc.); *Choanephora* blight (e.g., associated with *Choanephora cucurbitarum*, etc.); common rust (e.g., associated with *Puccinia pittieriana*, etc.); deforming rust (e.g., associated with *Aecidium cantensis*, etc.); gangrene (e.g., associated with *Boeremia foveata, Phoma exigua*, etc.); gray mold (e.g., associated with *Botrytis cinerea*, etc.); leak (e.g., associated with *Pythium aphanidermatum, Pythium deliense, Pythium* sp., *Pythium ultimum*, etc.); *Phoma* leaf spot (e.g., associated with *Phoma andigena*, etc.); *Pleospora herbarum* (e.g., associated with *Phoma andigena*, etc.); *Pleospora herbarum* (e.g., associated with *Ploespora herbarum*, etc.); powdery mildew (e.g., from leaves, associated with *Colovinomyces cichoracearum*, etc.); *Rosellinia* black rot (e.g., associated with *Rosellinia* sp., etc.); *Septoria* blight (e.g., associated with *Septoria lycoperisici*, etc.); silver scurf (e.g., associated with *Helminthosporium solani*, etc.); skin spot (e.g., associated with *Polyscytalum pustulans*, etc.); stem rot (e.g., associated with *Sclerotium rolfsii*, etc.); *Thecaphora* smut (e.g., associated with *Thecaphora solani*, etc.); *Ulocladium* blight (e.g., associated with *Ulocladium atrum*, etc.); white mold (e.g., associated with *Sclerotinia sclerotiorum*, etc.); zebra chip disease (e.g., from tubers, associated with *Liberibacter solanacearum*, etc.); and/or other factors.

Output features of Block S130 can, however, include other features associated with other disease-associated features, some examples of which are described in applications incorporated by reference.

2.2.11 Ecological-Impact

In more detail with respect to generation of features related to impact-associated features, Block S130 can include steps for generation of impact-associated ecological indices based upon bacteria-associated parameters and fungal-associated parameters, and then processing such network property parameters to generate features (e.g., as a unified "impact" parameter or feature), as another proxy for resilience/resistance of a soil microbiome community in relation to responses to various disease risks (described above). The impact parameter can represent a change in the co-occurrence and co-exclusion among microorganisms (e.g., changes in co-occurrence and co-exclusion of bacterial and fungal organisms represented in the sample dataset), where methods of generating co-occurrence and co-exclusion parameters are described in U.S. application Ser. No. 17/119,972 filed 11 Dec. 2020 and incorporated by reference above. In variations, the impact parameter can be determined based upon aggregation of all co-occurrence network properties and all co-exclusion network properties into a value that summarizes the effect that treatment or management practices has at each location.

For instance, an impact parameter can be derived from the distances (e.g., as a measure of dissimilarity) between the network properties (e.g., 16S network properties, ITS network properties) as a measure of the effect of a given input (e.g., treatment, management practice, product, etc.) on the bacterial and fungal network properties of the soil from one location. A linear regression model can be used to model the network properties, using location and timepoint only. The residuals of these models can then be projected onto a multidimensional space (e.g., using principal component analysis (PCA)).

In a specific example, an impact parameter characteristic of resilience can be derived from the scaled dissimilarity (distance) between the network properties (e.g., 16S network properties, ITS network properties) of treated and control samples in a given location, as a measure of the effect of a given input or practice (e.g., treatment, management practice, product, etc.) on the bacterial and fungal network properties of the soil from one location. A linear regression model can be used to model the network properties, using location and timepoint only. The residuals of these models are then projected onto a 10-dimensional space using principal component analysis (PCA), retaining 8 3% of variation in the residuals. In more detail, a method for determining impact parameters can include: modelling network properties from samples, using desired contextual parameters (e.g., location, time point), with collection of residuals; running a PCA on these residuals and generate a multi-dimensional location for each sample; and calculating the distance between the treatment and control centroids. For each location, the impact parameter is the weighted distance between treated and control samples of that location. Impact parameter values are thus distances (i.e. non-negative), and an impact parameter value of zero means that the treatment had negligible effect on the network properties of the soil microbiome. Furthermore, the magnitude of the impact parameter correlates with the magnitude of the effect of the particular input/practice.

Output features of Block S130 can, however, include other features associated with other resilience-associated features, some examples of which are described in applications incorporated by reference.

2.2.12 Ecological-Sustainable Productivity Index

Additionally or alternatively, the invention(s) can generate and apply a sustainable productivity index score. In embodiments, the sustainable productivity index score is crop-agnostic, using network properties and principal components of taxonomy and combining them to generate a single score. In variations, the sustainable productivity index can use microbiome functional annotations and/or other suitable annotations.

In embodiments, the sustainable productivity index can be defined based upon a proprietary database of soil samples from diverse crops with known management practices, where an increasing order of sustainability is defined based upon a set of predetermined management practices (e.g., conventional, organic and biodynamic). In embodiments, the system can include architecture for generating, training, and applying a combined supervised machine learning model, including regression and classification tasks to compute the index. In variations, the regression model can be constructed to predict a pre-score following expert-based criteria regarding management practices distances. In variations, the classification model can be constructed apply a management-dependent transformation over the pre-score. In examples, the sustainable productivity index quantitative values are in the range 0 to 100, going from lower to higher soil sustainability or productivity. In examples, the sustainable productivity index qualitative categories are in the range "infertility risk" to "natural farming", going from lower to higher soil sustainability or productivity.

In embodiments, the sustainable productivity index machine learning model can be applied to determine the score for any new/incoming soil sample, based upon one or more microbiome-derived properties defined above.

2.2.13 Overall Combinatorial Metrics

Furthermore, outputs of Block S130 can further implement steps for generation of combinatorial metrics based upon taxonomic annotations, functional annotations, and/or ecological indices generated as described above and/or in another suitable manner, which can be processed individually and/or in combination with other annotations and/or markers in relation to generation of agronomic indices in Block S140 below.

2.2.14 Refinement and Training

In relation to model architecture associated with training and refinement of machine learning models described, methods described in relation to Blocks S120 and S130 can be used to create training sets of data. As such, training data covering specific sample features and corresponding contextual information related to management practices and other perturbations (e.g., use of various products, environmental perturbations, other agricultural inputs, other practices, etc.) can be used to refine models for predicting effects of various practices and perturbations, and to guide future management practices in a sustainable manner.

In order to process such data, computing platforms implementing one or more portions of the method can be implemented in one or more computing systems, wherein the computing system(s) can be implemented at least in part in the cloud and/or as a machine (e.g., computing machine, server, mobile computing device, etc.) configured to receive a computer-readable medium storing computer-readable instructions.

To refine the model(s), the method 100 can include generating one or more training sets of data, from samples of the agriculture site(s) and/or other samples of other agriculture site(s), in order to train the artificial intelligence (AO/neural network (NN) model(s) in one or more stages of training, to identify features of interest from various inputs. In variations, generating training sets of data can include processing raw data and/or features taken from agriculture sites and/or crops with known characteristics (e.g., in relation to contextual and/or other data described above, in relation to agricultural inputs/practices applied in substantially controlled settings, etc.). Such training data can be tagged with associated crop-associated features, agriculture site statuses (e.g., health statuses) and/or other information (e.g., pertaining to nature of inputs/practices, etc.).

In examples, training data can include tagged contextual information, which can include environmental information, geolocation information, nature of products applied (e.g., dosing, duration of application, frequency of application), pathogens present at a site, and/or other suitable information.

Figure 3:
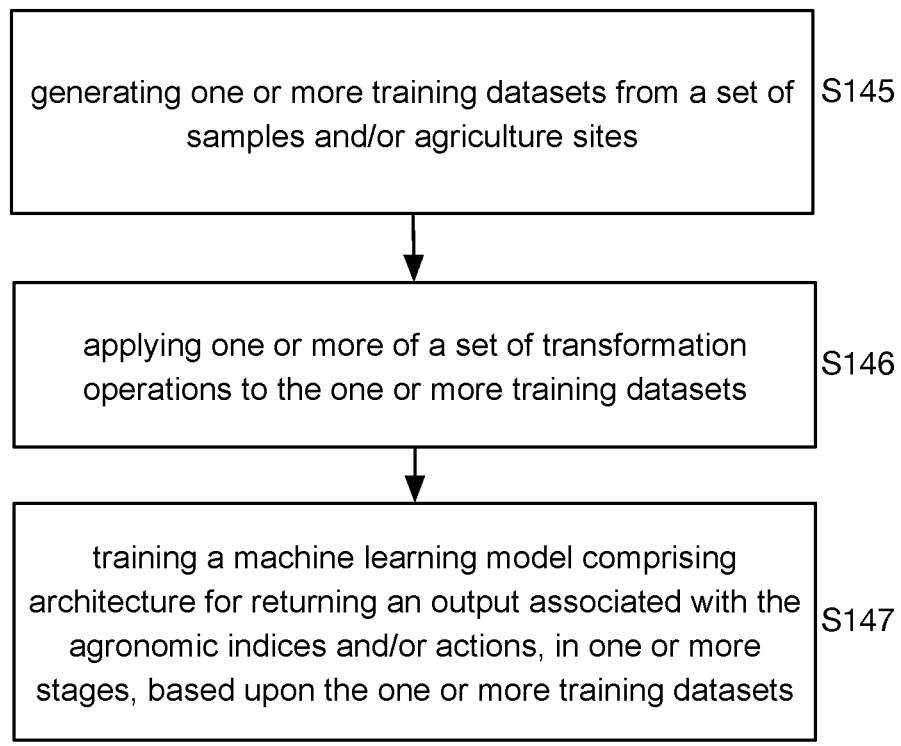
FIG. 3 depicts an embodiment of a portion of a workflow of a method for evaluating and predicting crop features with respect to training and refining developed models.

Training sets of data can include raw sequencing data, transformed sequencing data (e.g., according to transformation operations described above), and/or other suitable data. As such, as shown in FIG. 3, the method 100 can include: generating one or more training datasets S145 from a set of agriculture sites and/or crops (e.g., sites different from those in step S110, sites overlapping with those in step S110), the training datasets corresponding to features (e.g., of taxonomic annotations, of functional annotations, of ecological indices, etc.) in association with statuses and/or inputs or practices experienced by the agriculture site(s) and associated crops; applying one or more of a set of transformation operations to the one or more training datasets (e.g., using one or more operations described above) S146; and training a machine learning model comprising architecture for returning at least one of the set of unique signatures and the analysis, in one or more stages, based upon the one or more training datasets S147. Additional details are provided below.

For instance, in relation to generation of training datasets, the method can include generating taxonomic annotations, functional annotations, ecological indices, agronomic indices and other features upon samples from agriculture sites (or other sites) where statuses and/or perturbations are known. Additionally or alternatively, first training datasets can be generated from network properties/emergent properties and other features upon processing samples from agriculture sites (or other sites) known to be at baseline state. The model can be trained based upon the first training datasets. Then, the site(s) and/or associated crops can be intentionally perturbed in some manner, with subsequent sample acquisition and processing used to generate second training datasets for refining the model. This process can be repeated any suitable number of times. As such, training data can be developed in multiple stages. In relation to multiple stages of training, the method 100 can refine models based upon incorrect classification of outputs (e.g., mis-characterized statuses and/or perturbations).

Furthermore, combinatorial features (e.g., combination features derived from one or more individual network properties, one or more community properties, one or more taxonomic properties, and/or other suitable properties) can be used for training. In more detail, features may be transformed either individually or in combination before being processed by the model(s). As an example of an individual feature transformation, a feature derived from a transform of a co-exclusion feature might be used instead of or in addition to the co-exclusion feature itself. As an example, a combinatorial feature can be derived from synchronous co-exclusion of a pair of organisms and co-inclusion of a pair of organisms (e.g., where occurrence together is a feature). Additionally or alternatively, combinatorial features based upon bacteria-associated parameters and fungal-associated parameters can be used as inputs (e.g., as a unified "impact" parameter or feature). For instance, an impact parameter can be derived from the scaled dissimilarity (distance) between the network properties (e.g., 16S network properties, ITS network properties), as described in U.S. App. No. 1 7/119, 972 filed 11 Dec. 2020, incorporated by reference above.

Additionally or alternatively, dynamic aspects (e.g., changes over time in features, changes in frequency between instances of respective features, other temporal aspects, other frequency-related aspects, etc.) of features derived from the samples can be used to predict or otherwise anticipate statuses. As such, models can be implemented to prevent adverse statuses of the agriculture sites to prevent root causes of failure and/or break chains of events that could lead to a cascade of agriculture site problems.

Models can be developed and trained for real-time analyses and/or historical analyses. In relation to real-time analyses, the models can be refined for rapid classification (e.g., with node reduction, with reduced thresholds, with lower confidence, etc.). In relation to historical analyses, the models can be refined for detailed classification (e.g., without node reduction, with higher thresholds for classification predictions, with higher confidence, etc.).

In embodiments, the method 100 can thus include training a model configured to process input features and return predicted characterizations of agronomic indices and/or associated features of the agriculture site, wherein training the model comprises: collecting a training dataset derived from samples, the training dataset corresponding to training samples subject to at least one of a management practice and a perturbation (e.g., substance applied, environmental control condition, etc.) at the agriculture site as well as control samples without undergoing the input factor; applying one or more of a set of transformation operations to the training dataset; and training the model with the training dataset, the model comprising architecture for returning the analysis, in one or more stages. Training and refinement can be further applied to outputs for generation of agronomic indices and recommended actions, as described in further detail below.

While embodiments, variations, and examples of models (e.g., in relation to inputs, outputs, and training) are described above, models associated with the method can additionally or alternatively include other blocks for statistical analysis of data and/or machine learning architecture.

Statistical analyses and/or machine learning algorithm(s) can be characterized by a learning style including any one or more of: supervised learning (e.g., using back propagation neural networks), unsupervised learning (e.g., K-means clustering), semi-supervised learning, reinforcement learning (e.g., using a Q-learning algorithm, using temporal difference learning, etc.), and any other suitable learning style.

Furthermore, any algorithm(s) can implement any one or more of: a regression algorithm, an instance-based method (e.g., k-nearest neighbor, learning vector quantization, self-organizing map, etc.), a regularization method, a decision tree learning method (e.g., classification and regression tree, chi-squared approach, random forest approach, multivariate adaptive approach, gradient boosting machine approach, etc.), a Bayesian method (e.g., naïve Bayes, Bayesian belief network, etc.), a kernel method (e.g., a support vector machine, a linear discriminant analysis, etc.), a clustering method (e.g., k-means clustering), an associated rule learning algorithm (e.g., an Apriori algorithm), an artificial neural network model (e.g., a back-propagation method, a Hopfield network method, a learning vector quantization method, etc.), a deep learning algorithm (e.g., a Boltzmann machine, a convolution network method, a stacked auto-encoder method, etc.), a dimensionality reduction method (e.g., principal component analysis, partial least squares regression, etc.), an ensemble method (e.g., boosting, boot strapped aggregation, gradient boosting machine approach, etc.), and any suitable form of algorithm.

2.3 Methods—Generating Agronomic Indices

Block S140 recites: generating values of a set of agronomic indices based on the set of microbiome-associated features, which functions to transform outputs of Block S130 into features falling into one of multiple (e.g., three) "agronomic" categories: biosustainability, health, and nutrition. Outputs can be returned in relation to quantitative values and/or qualitative values (e.g., based upon the quantitative values). In an example, quantitative values can be transformed to a qualitative scale of 5 quintiles: very low, low, medium, high, very high. However, output values of the agronomic indices can be provided in another suitable manner.

2.3.1 Agronomic Indices: Biosustainability

1. Biosustainability: In examples, the invention(s) can generate and implement multiple (e.g., 3, less than 3, more than 3) metrics characterizing diversity of sample species and/or metabolic functions present in the sample(s) from the agricultural sites, as well as vulnerability of the system based on estimation of microbiome resistance. Biosustainability indices are biomarkers of the ecosystem in which a site is based, and related to management practices. In examples, three biosustainability indices can be generated:

1A. Biodiversity (species richness, evenness, and equilibrium of species): outputs can be generated from Shannon diversity characterization, based on taxonomic assignment. However, other outputs can additionally or alternatively be generated based upon evaluation of richness, phylogenetic entropy (e.g., based on a proprietary database of soil samples), or any other method(s).

1B. Functionality (capability of communities to perform one or more functions): outputs can be generated from Shannon diversity of the metagenomic functions predicted, but it could be any other diversity metric based on the functions.

1C. Resistance (stress adaptation, ability of communities or populations to remain unchanged when stressed by a disturbance): outputs can be generated from the transitivity of the bacterial network, but again could be any other suitable network property. Exemplary species grouped according to their relationship with metabolisms associated with capability to withstand stress conditions include: Exopolysaccharide production capabilities (e.g., with nutrient trapping capabilities, salinity protection capabilities, drought protection capabilities, etc.); heavy metal solubilization (e.g., with bioremediation capabilities, detoxification capabilities, heavy metal stress alleviation capabilities, etc.); salt tolerance capabilities (e.g., with salinity protection capabilities, root growth promotion capabilities, etc.); siderophore production capabilities (e.g., with association iron availability, biofertilizer capabilities, etc.); ACC deaminase capabilities (e.g., with pathogen protection capabilities, with salinity protection capabilities, with drought protection capabilities, etc.); salicylic acid capabilities (e.g., with drought protection capabilities, with salinity protection capabilities, with heavy metal stress alleviation capabilities, etc.); abscisic acid production (e.g., with growth regulation capabilities, with plant resistance capabilities, with yield increase capabilities, etc.).

In examples, low value indices are indicators of aggressive practices, while high value indices are linked to sustainable practices.

As such, generating values of the biosustainability index can include generating a biodiversity value representing species richness, a functionality value representing metagenomic functions, and a resistance value representing stress adaptation of communities represented in the sample dataset.

2.3.2 Agronomic Indices: Health

2. Health: In examples, the invention(s) can generate and implement multiple (e.g., 4) metrics characterizing the role of microorganisms in plant health and yield, as defined by a balance between pathogens, biocontrol agents, and/or other plant growth promotors:

2A. Healthiness (crop health according to detected pathogens): In examples, the invention(s) include steps for generating a score for each disease-risk factor based on the crop-specific pathogen lists. The score (quintile) combines the relative abundance of the disease-risk factor and the resistance score of the soil. Then, based on the quintiles of the minor and major diseases per crop, the invention(s) include architecture for calculating a health score as follows:

At least one major disease in sample at level 5 (maximum quintile), then score=1.

At least one major disease in sample at level 4, then score=2

At least one major disease in sample (not zero), then score=3

At least one minor disease in sample (not zero), then score=4 no disease in sample, then healthiness score=5

In addition to just using the resistance score (i.e., based upon transitivity of networks described above), the invention(s) can further implement transitivity of fungal networks, and co-exclusion proportions in both (bacterial & fungal) networks. Additionally or alternatively, the invention(s) can generate and apply a health index score that is crop-agnostic (i.e. not using disease abundances, but instead, using network properties and principal components of taxonomy and combining them to generate a single score, examples of which are defined above in embodiments, variations, and examples, and further shown in applications incorporated by reference.

In further variations, the invention(s) can be applied to soils known to suppress certain diseases in contrast to soils that allow the diseases to occur, thereby enabling identification of specific taxa or network properties that explain the suppression of the disease pathogens.

In variations, health indices (e.g., soil health indices) can be generated from samples having known management practices (e.g., conventional, organic, biodynamic, etc.), from a wide variety of geographies and crop types (e.g., almond, banana, corn, horticolas, lettuce, mustard, olive, onion, peppers, pimentos, rapeseed, tomatoes, vineyard, wheat, other, etc.). In examples, the dataset generated from samples was split into training and test datasets, and the data was modeled (e.g., using a LASSO Ridge regression, using 16S and ITS data, enriched and depleted, network properties), thereby generating coefficients for modularity, transitivity, assortativity, p-length, and other properties. Coefficients represent the amount by which the health index increases/decreases when a given variable increases by one standard deviation, and can be tagged to indicated interactions between different variables. Representatives health indices and probability densities for conventional, organic, and biodynamic management practices are shown in FIG. 2B.

Variations of models can include accounting for network properties and principal components from taxonomic annotation (e.g., to improve model fit), where health indices can be divided categorically (e.g., in ranges), characterizing 16S+ITS, 16S only, and ITS only. As such, models for generating and returning health index values based upon features generated in Block S120 can be constructed to inform actions executed in Block S150.

In relation to health indices, the method can further include generation of sustainable productivity indices as a proxy for health, where the sustainable productivity indices can be generated as described and/or in applications incorporated by reference.

2B. biocontrol species (microbial species grouped according to the type of pests they encounter, capability of preventing pathogenic species from taking hold or proliferating): The invention(s) can generate relative abundances of the microorganisms on each of these categories: Fungicides, Bactericides, Insecticides, and Nematicides. Additionally or alternatively, the invention(s) can process and apply network properties, since a soil with a high fungal network transitivity and a strong biocontrol set of species is going to be even more resilient to external disruptions (e.g., abiotic, biotic, etc.) than one with just the biocontrol species present but not a high network transitivity.

2C. phytohormone producing species (microbial species grouped according to the type of phytohormone they generate): The invention(s) include steps and architecture for generating relative abundance of microorganisms that produce: Cytokinin production (e.g., with cell proliferation hormone generation, with cell differentiation hormone generation, etc.), Auxin production (e.g., with cell division hormone generation, with stem elongation hormone generation, etc.), and Gibberellin production (e.g., with stem elongation hormone generation, with germination hormone generation, with flowering hormone generation, etc.) for instance, in terms of percentages).

2D. stress sensing and tolerance species (microbial species grouped according to their ability to produce metabolites that help plants withstand stress conditions): The invention(s) include steps and architecture for relative abundance of microorganisms that produce: ACC deaminase, exopolysaccharide production, heavy metal solubilization, salt tolerance, siderophore production, salicylic acid, and abscisic acid.

As such, generating values of the health index can include generating a healthiness value associated with detected pathogens, a biocontrol value representing capability of preventing pathogenic species effects at the agriculture site, a phytohormone value representing generated phytohormones, and a stress value representing metabolites associated with stress withstanding.

2.3.3 Agronomic Indices: Nutrition

3. Nutrition: The invention(s) include steps and architecture for characterizing the potential of soil microorganisms to cycle nutrients and to increase the bioavailability of nutrients for plants). Examples of relative abundance of enzymes from predicted metagenomes are described in applications incorporated by reference.

Additionally or alternatively, the inventions can include steps and architecture for processing and applying features related to one or more of:

Carbon (as the basis of soil fertility with release of nutrients for plant growth, promotion of structure and health of soils, and buffer against harmful substances): with identification of new enzyme activities/taxa associated to the potential to sequester carbon. In examples, samples from biodynamic soils (e.g., with no-tilling) with high capacity to sequester carbon, and from traditional soils (e.g. tilling) with low capacity to sequester Carbon, can be processed according to the invention(s) described.

Any nutrient: by determining metabolic fluxes, not just relative abundances of enzyme activities; by determining percentage of enzymes present from a given pathway (not just abundance); by determining function representation in microorganisms from each of the modules in networks. For instance, indices can be related to one or more of: pathways that directly benefit plant nutrition, pathways that take up nutrients from the soil, nitrogen pathways, phosphorus pathways, minor compounds (e.g., sulfur, calcium, chlorine, magnesium, iron, manganese, zinc, copper, and/or other nutrients.

As such, generating values of a nutrition index can include generating values of nutrient dynamics represented in the sample dataset.

In further examples, outputs of the invention(s) can be combined, presented, and/or applied in relation to physicochemical properties of samples or crops, to return biology indexes and physical/chemical indexes, an example of which is shown in applications incorporated by reference.

2.4 Methods—Actionable Outcomes

In some variations, the method 100 can additionally or alternatively include Block S150, which recites: executing an action for producing a desired outcome in relation to the agriculture site, with respect to one or more specific soil types and/or one or more specific crops, based upon the set of agronomic indices. Block S150 functions to process outputs of prior steps in order to generate insights and/or execute actions that can improve productivity, correct issues, and/or increase sustainability of practices at the agriculture site(s) being assessed. In particular, agricultural inputs and management practices can have inconsistent field performance with uninformed application, where, in relation to some inputs, different strains and species can have different functional performance under specific environmental and ecological conditions. As such, Block S150 can provide agricultural inputs and implement management practices in an informed manner that is targeted to specific crops, soil types, and/or environmental conditions.

In variations, executing the action can include generating digital objects encoding instructions for controlling apparatus associated with an operator managing the agriculture site. In variations, executed actions can include or be associated with one or more of: maintaining a status of an agriculture site by providing guidance for maintaining current management statuses and/or products used; responding to an issue detected at the agriculture site(s) being assessed (e.g., in relation to pathogen presence or increased abundance of a detrimental microorganism, in relation to decreased abundance of a beneficial microorganism, in relation to correcting a perturbation, in relation to adjusting application of a product at the agriculture site, implementing protective measures against environmental effects, etc.); responding to or otherwise correcting other undesired statuses at one or more agriculture sites being monitored; providing information regarding site characteristics to a manager/operator/other entity associated with the agriculture site(s); performing decision-making guidance (e.g., in relation to analyses indicative of sustainability of practices, in relation to long term effects of use of one or more products, etc.); and performing other suitable actions.

In generating recommended actions, step S150 can include returning notifications or other information derived from the analyses and other outputs of step S140 in a visual format, in an audio format, in a haptic format, and/or in any other suitable observable format, to a manager, operator, and/or other entity associated with the agriculture site(s) being assessed. As such, variations of Block S150 can include generating digital objects (e.g., in visual data formats, in audio data formats, in haptic data formats) or instructions for generating digital objects, in communication with client devices (e.g., mobile devices or other devices that are associated with a manager, operator, and/or other entity associated with the agriculture site(s)), where the client devices include visual output components (e.g., a display), audio output components (e.g., speaker), haptic output components (e.g., vibrators), and/or any other suitable components. Client devices can also include input components (e.g., keypads, touch displays, microphones, joysticks, mice, etc.) such that the managers, operators, or other entities associated with the agriculture site(s) can communicate inputs (e.g., commands) related to the generated analyses.

An example output report can provide guides for major and minor nutrients, providing insights into specific characteristics for a site or crop of a customer.

For instance, guides for nitrogen pathways can include a description: Nitrogen plays a major role in achieving the maximum yield potential and is an essential constituent of chlorophyll. The degradation of organic nitrogen and nitrogen fixation by microorganisms, supplies available forms of nitrogen for both plants and other microbes. Low values indicate that the nitrogen naturally supplied by microbes to plants is low; therefore plant growth is stunted and slowed; Inorganic nitrogen release: mineralization, or the microbial transformation of organic nitrogen compounds to inorganic nitrogen compounds that serve as plant nutrients; Inorganic nitrogen consumption: immobilization, or the microbial transformation of inorganic nitrogen compounds to organic forms, which are not readily accessible for uptake by plants; Inorganic nitrogen cycle health: the conversion of nitrogen into multiple chemical forms as it circulates. These processes include ammonification, nitrification, denitrification, and anaerobic ammonia oxidation.

Guides for phosphorus pathways can include a description: phosphorus is a fundamental nutrient required in the regulation of protein synthesis and plant growth. It enhances the development of roots, while its deficiency leads to stunted growth, dark purple color of leaves and inhibition of flowering. Low values indicate that the microbial processes that make phosphorus available for plants are low; Inorganic phosphorus solubilization: certain soil microorganisms are capable of dissolving insoluble phosphorus from minerals and rocks. They convert insoluble phosphorus in the soil into a form that plants can access, improving their growth and yield; Inorganic phosphorus consumption: Immobilization of inorganic phosphorus into organic phosphorus. Inorganic phosphorus may represent less than 10% of the total content of this component in the soil, although plants mainly uptake phosphorus in this form from the soil solution Organic phosphorus assimilation: organic phosphorus may represent from 1 5% to 80% of the total content of this element in the soil. During mineralization process, organic phosphorus replenishes the phosphorus solution.

Guides for potassium pathways can include a description: Potassium pathways: potassium is a regulator of metabolic activities especially those involved in producing proteins and sugars and regulating crop evotranspiration. When bio-available potassium is deficient it causes flabby plants and sensitivity to droughts. Potassium may further alter the assimilation of nitrogen and phosphorus metabolism. Low values indicate that the microbial processes that make potassium available for plants are low; Inorganic potassium solubilization: certain soil microorganisms are capable of dissolving insoluble potassium from minerals and rocks. They convert insoluble potassium in the soil into a form that plants can access, improving their growth and yield; Potassium consumption: both plants and microbes require potassium to their functioning. High values indicate an optimal potential of microbes to assimilate this nutrient.

Guides can include a description of minor compounds (e.g., elements with less influence on the crop's nutritional status yet necessary for the correct development of some plant functions): Sulfur: sulfur is an essential nutrient that plants need in sufficient amounts to maintain good health and achieve high yields. It is found in organic matter, but is not available to plants in this form, so it must go through mineralization and cycling processes. It is also crucial for chlorophyll formation and it is an active agent in the metabolism of nitrogen. Medium to high values indicate a healthy balanced functioning of the sulfur cycle; Calcium: calcium contributes to soil fertility by regulating the assimilation of other nutrients. Calcium deficiency symptoms in crops are usually caused by low calcium availability or water stress which result in low transpiration rates. High microbial transport of calcium helps to maintain the physical properties of the soil and to stabilize soil structure; Chlorine: chlorine is an important micronutrient that takes part in several physiological metabolic processes such as in disease resistance and tolerance, as well as in fruit quality and crop yields. Medium to high levels of microbial transport helps to sustain a good equilibrium of this micronutrient. Soils may become deficient in chlorine if rainfall is high or plants are irrigated too frequently, especially in sandy soils; Magnesium: magnesium is a nutrient involved in many enzyme activities and the structural stabilization of tissues. It plays a key role in phosphorus transportation to where it is needed and the use of iron. It is also crucial for the uptake of nutrients and for nitrogen fixation. High values of magnesium transport by microbes are optimal; Iron: iron is the fourth most abundant element found in soil though it is largely present in forms that cannot be taken up by plants. Previously solubilized Iron is essential for microbial enzymatic structures and activities such as nitrogen fixation. Medium to high values indicate a sufficient potential for iron microbial assimilation; Manganese: manganese contributes to some biological systems including photosynthesis, respiration and nitrogen assimilation. Manganese deficiency is a widespread problem, most often occurring in sandy soils, organic soils with a pH above 6 and heavily weathered tropical soils. Microbes are indicators of manganese problems through alterations of import/export processes to their cells (therefore, low or high values are not optimal); Zinc: zinc is a micronutrient that is needed in small amounts, yet it is crucial to plant development. It is key for the constitution of many proteins and enzymes, and is essential for hormone production processes. Deficiency in zinc can reduce crop yield by over 20% before any visual symptoms of the deficiency occur. Microbes are indicators of zinc problems through alterations of import/export processes to their cells (therefore, low or high values are not optimal);

Copper: copper is one of the micronutrients needed in very small quantities by plants, rarely limiting, and excesses can be toxic. Iron toxicities can have a negative impact on crop growth and quality. Microbes are good indicators of copper excesses through export mechanisms. High values indicate potential copper excesses.

An example output report of the invention(s) is shown in applications incorporated by reference and FIGS. 2A-2F.

Additionally or alternatively, generating recommended actions can include generating control instructions for apparatus (e.g., machinery, robotic apparatus configured to traverse an agricultural site, other apparatus) configured to execute computer-readable instructions for management of the agriculture site(s). In variations, control instructions can involve instructions for controlling operation modes of one or more of: watering subsystems (e.g., in relation to water distribution through conduits and/or sprinklers to the agriculture site(s)); product delivery subsystems in communication with watering subsystems (e.g., delivery subsystems in communication with watering subsystems through fluidic components, valves, etc.); robotic crop handling subsystems (e.g., in relation to removal of pathogen-affected crop portions); robotic crop picking subsystems (e.g., in relation to automated harvesting at optimal time periods in relation to improving production, in relation to efficiency of new production generation post-harvesting, in relation to minimization of wasted product, etc.); robotic nutrient delivery or pesticide delivery subsystems (e.g., in relation to initiating delivery, in relation to stopping delivery, in relation to adjusting frequency of delivery, in relation to adjusting delivery dosages, etc.); greenhouse subsystems; temperature control subsystems (e.g., in relation to modes for controlling environmental temperature of the agriculture site, etc.); light control subsystems (e.g., in relation to modes for controlling environmental light of the agriculture site, in relation to transitioning between on and off states, in relation to light spectrum delivered, etc.); gas environment subsystems (e.g., in relation to modes for controlling environmental gas composition of the agriculture site, etc.); humidity control subsystems (e.g., in relation to modes for controlling environmental humidity levels of the agriculture site, etc.); pressure control subsystems (e.g., in relation to modes for controlling environmental pressure of the agriculture site, etc.); and other suitable subsystem(s) of the agriculture site(s). Additionally or alternatively, Block S150 can include generation of control instructions for automated vehicle platforms associated with controlling vehicles associated with the agriculture site(s), with respect to surveying, management, and/or other operation modes.

In examples, instructions for controlling operation modes of watering subsystems (e.g., in relation to water distribution through conduits and/or sprinklers to the agriculture site(s)) can be automatically executed in response to detected states of undesired watering levels based upon model outputs from other steps of the method. As such, controlling operation modes can include transitioning the watering subsystems between various states of flow, on-off states, etc. Control can be modulated in relation to constraints associated with water usage (e.g., times of drought, in relation to water usage incentives, etc.).

In examples, instructions for controlling operation modes of product delivery subsystems (e.g., delivery subsystems in communication with watering subsystems through fluidic components, valves, etc.) can be automatically executed in response to detected states of undesired supplement levels based upon model outputs from other steps of the method. As such, controlling operation modes can include transitioning the delivery subsystems between various states of product dosage, flow rates, on-off states, etc.

In examples, instructions for controlling operation modes of robotic crop handling subsystems (e.g., in relation to removal of pathogen-affected crop portions), robotic crop picking subsystems (e.g., in relation to automated harvesting at optimal time periods in relation to improving production, in relation to efficiency of new production generation post-harvesting, in relation to minimization of wasted product, etc.), robotic nutrient delivery or pesticide delivery subsystems (e.g., in relation to initiating delivery, in relation to stopping delivery, in relation to adjusting frequency of delivery, in relation to adjusting delivery dosages, etc.), and/or other robotic subsystems can be automatically executed in response to detected states of harvesting time, pathogen detection, nutrient states, pest presence, and/or other factors based upon model outputs from other steps of the method. As such, controlling operation modes can include transitioning the robotic subsystems between various states of actuation.

In examples, instructions for controlling operation modes of greenhouse subsystems, temperature control subsystems (e.g., in relation to modes for controlling environmental temperature of the agriculture site, etc.), light control subsystems (e.g., in relation to modes for controlling environmental light of the agriculture site, in relation to transitioning between on and off states, in relation to light spectrum delivered, etc.), gas environment subsystems (e.g., in relation to modes for controlling environmental gas composition of the agriculture site, etc.), humidity control subsystems (e.g., in relation to modes for controlling environmental humidity levels of the agriculture site, etc.), pressure control subsystems (e.g., in relation to modes for controlling environmental pressure of the agriculture site, etc.), and/or other environmental control subsystems can be automatically executed in response to detected states of environmental conditions suited to or unsuited for desired outcomes, and/or other factors based upon model outputs from other steps of the method. As such, controlling operation modes can include transitioning the environmental control subsystems between various states of temperature control, light control, gas control, humidity control, pressure control, and/or other environmental control. Control can be modulated in relation to constraints associated with power usage (e.g., times of peak demand, in relation to demand incentives, etc.).

Additionally or alternatively, step S150 can include generation of control instructions for automated vehicle platforms associated with controlling vehicles associated with the agriculture site(s), with respect to surveying, management, and/or other operation modes.

Block S150 can include or be associated with executing the recommended action through electronic communication with one or more subsystems described above, which functions to automatically execute recommended actions in order to reduce operator workload in relation to agriculture site management. Executed actions can include or be associated with one or more of: maintaining a status of an agriculture site by providing guidance for maintaining current management statuses and/or products used; responding to an issue detected at the agriculture site(s) being assessed (e.g., in relation to pathogen presence, in relation to detrimental microorganism presence, in relation to correcting a perturbation, in relation to adjusting application of a product at the agriculture site, implementing protective measures against environmental effects, etc.); responding to or otherwise correcting other undesired statuses at one or more agriculture sites being monitored; maintaining or improving desired statuses at one or more agriculture sites being monitored (e.g., in relation to biocontrol microorganism presence, in relation to stress tolerance microorganism presence, in relation to plant growth promoter microorganism presence, in relation to nutrient metabolizing microorganism presence, etc.); providing information regarding site characteristics to a manager/operator/other entity associated with the agriculture site(s); performing decision-making guidance (e.g., in relation to analyses indicative of sustainability of practices, in relation to long term effects of use of one or more products, etc.); and performing other suitable actions, as described above in embodiments, variations, and examples of agriculture site management control and notification/report delivery. Embodiments, variations, and examples of actions are further described in U.S. application Ser. No. 17/119,972 filed 11 Dec. 2020, incorporated by reference above.

3. System

Figure 4:
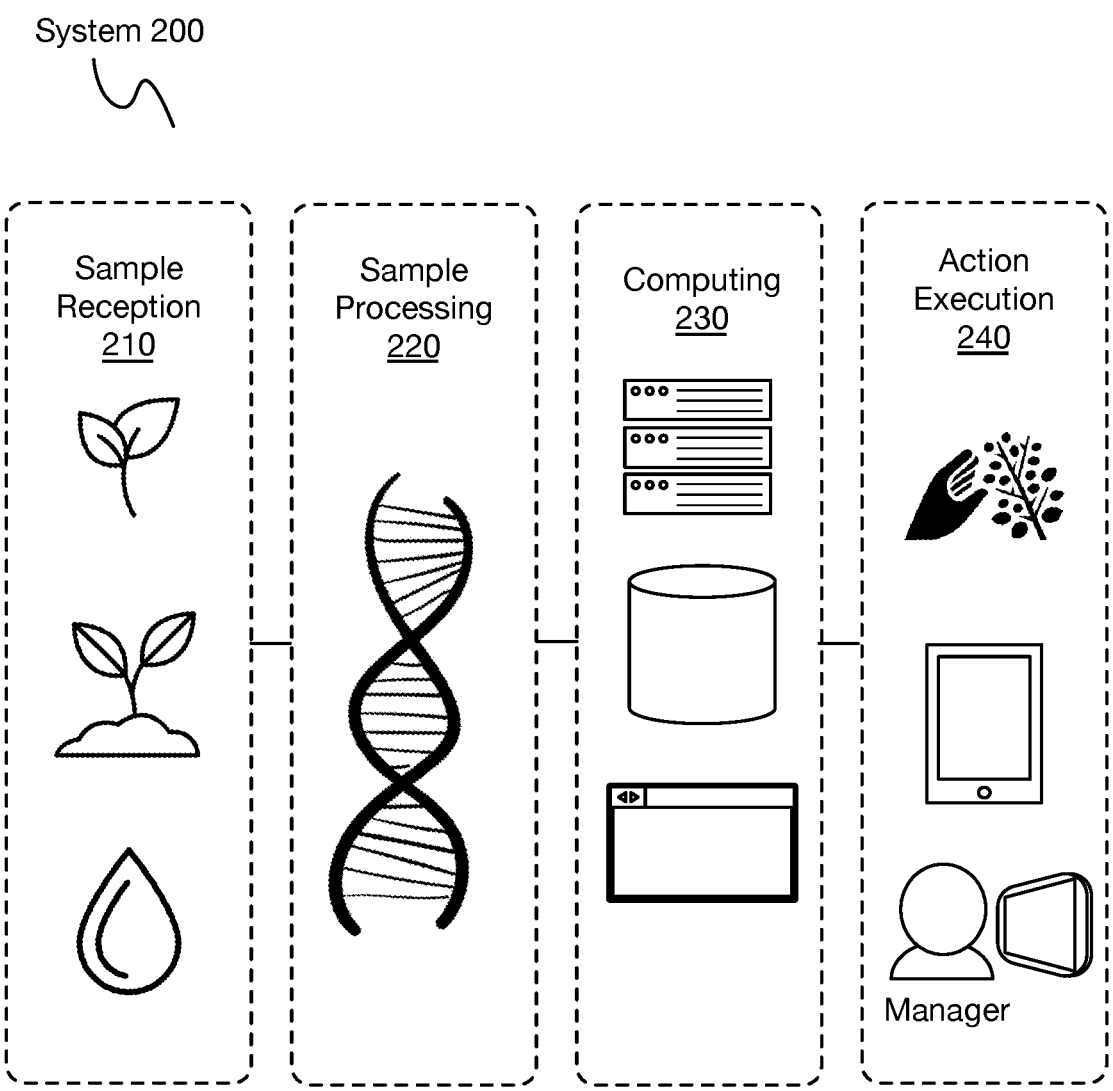
FIG. 4 depicts an embodiment of a system for generating and applying agronomic indices.

As shown in FIG. 4, a system 200 for characterization and improvement of an agricultural site includes: one or more sample reception subsystems 210; one or more sample processing subsystems 220 in communication with the sample reception subsystems 210; a computing platform 230 comprising one or more processing subsystems comprising non-transitory computer-readable medium comprising instructions stored thereon, that when executed by the processing subsystems perform one or more steps of methods described above; and one or more action execution subsystems 240 configured to execute actions informed by processes of the computing platform 230. In variations, the action execution subsystems 240 can be configured to execute control instructions generated by the computing platform 230, where control instructions can involve instructions for controlling operation modes of one or more of: watering subsystems (e.g., in relation to water distribution through conduits and/or sprinklers to the agriculture site(s)); product delivery subsystems in communication with watering subsystems (e.g., delivery subsystems in communication with watering subsystems through fluidic components, valves, etc.); robotic crop handling subsystems (e.g., in relation to removal of pathogen-affected crop portions); robotic crop picking subsystems (e.g., in relation to automated harvesting at optimal time periods in relation to improving production, in relation to efficiency of new production generation post-harvesting, in relation to minimization of wasted product, etc.); robotic nutrient delivery subsystems (e.g., in relation to initiating delivery, in relation to stopping delivery, in relation to adjusting frequency of delivery, in relation to adjusting delivery dosages, etc.); greenhouse subsystems; temperature control subsystems (e.g., in relation to modes for controlling environmental temperature of the agriculture site, etc.); light control subsystems (e.g., in relation to modes for controlling environmental light of the agriculture site, in relation to transitioning between on and off states, in relation to light spectrum delivered, etc.); gas environment subsystems (e.g., in relation to modes for controlling environmental gas composition of the agriculture site, etc.); humidity control subsystems (e.g., in relation to modes for controlling environmental humidity levels of the agriculture site, etc.); pressure control subsystems (e.g., in relation to modes for controlling environmental pressure of the agriculture site, etc.); and other suitable subsystem(s) of the agriculture site(s).

Embodiments of the system 200 are configured to perform one or more portions of methods described above; however, variations of the system 200 can be configured to perform other suitable methods.

4. Conclusions

Embodiments of the invention(s) can include every combination and permutation of the various system components and the various method processes, including any variants (e.g., embodiments, variations, examples, specific examples, figures, etc.), where portions of embodiments of the methods and/or processes described herein can be performed asynchronously (e.g., sequentially), concurrently (e.g., in parallel), or in any other suitable order by and/or using one or more instances, elements, components of, and/or other aspects of the system and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the methods and/or systems can be embodied and/or implemented at least in part as a machine configured to receive a computer-readable medium storing computer-readable instructions. The instructions can be executed by computer-executable components that can be integrated with embodiments of the system. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the methods, systems, and/or variants without departing from the scope defined in the claims. Variants described herein not meant to be restrictive. Certain features included in the drawings may be exaggerated in size, and other features may be omitted for clarity and should not be restrictive. The figures are not necessarily to scale. The absolute or relative dimensions or proportions may vary. Section titles herein are used for organizational convenience and are not meant to be restrictive. The description of any variant is not necessarily limited to any section of this specification.

What is claimed is:

1. A method for generating agronomic indices and executing one or more actions in response to said agronomic indices at an agriculture site, the method comprising:

receiving a set of samples associated with the agriculture site;

generating a sample dataset upon processing the set of samples with a set of sample processing operations comprising spiking the set of samples with a synthetic construct comprising a structure of: [16S Forward Primer][ITS Forward Primer][Random Sequence comprising a 16S sequence and an ITS sequence][16S Reverse Complement Primer][ITS Reverse Complement Primer];

generating a set of microbiome-associated features upon performing a set of transformation operations upon the sample dataset, wherein the set of microbiome-associated features comprises a first subset of taxonomic annotations, a second subset of functional annotations and a third subset of ecological indices, wherein generating the set of microbiome-associated features comprises simultaneously generating absolute concentrations of each bacterial organism and each fungal organism represented in the set of samples, based upon a copy number of the synthetic construct;

generating values of a set of agronomic indices based upon the set of microbiome-associated features; and executing an action for improving fertility at the agriculture site, based upon the set of agronomic indices.

2. The method of claim 1, wherein the set of samples comprise at least one of: a soil sample, a root sample, a foliage sample, a liquid sample, and a crop-derived sample.

3. The method of claim 1, wherein the set of sample processing operations comprises: a nucleic acid extraction operation; a library preparation operation upon amplification and sequencing of target regions comprising a 16S region and an ITS region to generate a set of identified sequences; a filtering operation with filtering of chimera sequences and clustering of non-singleton sequences of the set of identified sequences; a mapping of sequences output by the filtering operation to operational taxonomic units (OTUs) with an identity threshold; and a tagging operation wherein the set of identified sequences tagged with contextual data associated with a management practice at the agriculture site.

4. The method of claim 1, wherein the first subset of taxonomic annotations comprises annotations derived from: OTUs; amplicon-sequence variants (ASVs), taxonomic quantification values generated upon addition of a synthetic spike to the set of samples; diversity metrics capturing alpha and beta diversity of taxonomic groups; and abundance parameters comprising bacterial abundance and fungal abundance parameters.

5. The method of claim 4, wherein the second subset of functional annotations comprises annotations derived from: nutrient metabolic pathways generated from predicted metagenomic functional factors; plant growth promotor-associated factors; biocontrol species factors; and functional diversity metrics.

6. The method of claim 5, wherein the second subset of functional annotations comprises features associated with carbon pathways, nitrogen pathways, phosphorus pathways, and potassium pathways.

7. The method of claim 6, wherein the second subset of functional annotations further comprises features associated with iron pathways, zinc pathways, manganese pathways, sulfur pathways, calcium pathways, copper pathways, chlorine pathways, and magnesium pathways.

8. The method of claim 5, wherein the second subset of functional annotations comprises functional features associated with salt tolerance, heavy metal solubilization, indoleacetic acid production, cytokinin production, gibberellin production, ACC deaminase, exopolysaccharide production, abscisic acid, salicylic acid, and siderophore production.

9. The method of claim 5, wherein the second subset of functional annotations comprises functional features associated with fungicide biocontrol agents, bactericide biocontrol agents, nematicide biocontrol agents, and insecticide biocontrol agents.

10. The method of claim 4, wherein the third subset of ecological indices comprises: a resilience index derived from transitivity of bacterial networks and fungal networks represented in the set of samples.

11. The method of claim 10, wherein generating the resilience index comprises generating a network property dataset from the sample dataset, transforming a first grouping of positive pairs of organisms and a second grouping of negative pairs of organisms represented in the sample dataset into co-inclusion parameters and co-exclusion parameters.

12. The method of claim 4, wherein the third subset of ecological indices comprises disease-risk indices associated with one or more of: rot, scab, wilt, blight, scurf, canker, wart, dot, spot, pit, blotch, rust, gangrene, mold, leak, mildew, and smut.

13. The method of claim 4, wherein the third subset of ecological indices comprises an impact parameter representing changes in co-occurrence and co-exclusion of bacterial and fungal organisms represented in the sample dataset.

14. The method of claim 4, wherein the third subset of ecological indices comprises a sustainable productivity index generated from a combination of network properties and principal components of taxonomy generated from the sample dataset.

15. The method of claim 1, wherein generating the set of microbiome-associated features comprises:
generating a set of training data streams from a set of training samples at the agriculture site;
applying one or more of the set of transformation operations to the set of training data streams corresponding to the first subset of taxonomic annotations, the second subset of functional annotations and the third subset of ecological indices in association with inputs and practices at the agriculture site;
creating a training dataset derived from the set of training data streams and the set of transformation operations; and
training a machine learning model comprising architecture for returning at least one of the set of microbiome-associated features and the analysis, in one or more stages, based upon the using the training dataset.

16. The method of claim 1, wherein generating values of a set of agronomic indices comprises generating values of a biosustainability index, values of a health index, and values of a nutrition index.

17. The method of claim 16, wherein generating values of the biosustainability index comprises generating a biodiversity value representing species richness, a functionality value representing metagenomic functions, and a resistance value representing stress adaptation of communities represented in the sample dataset.

18. The method of claim 16, wherein generating values of the health index comprises generating a healthiness value associated with detected pathogens, a biocontrol value representing capability of preventing pathogenic species effects at the agriculture site, a phytohormone value representing generated phytohormones, and a stress value representing metabolites associated with stress withstanding.

19. The method of claim 16, wherein generating values of the nutrition index comprises generating values of nutrient dynamics represented in the sample dataset.

20. The method of claim 1, wherein executing the action comprises applying of one or more of: a biofertilizer, a biostimulant, a biocontrol agent, an agent for hormone production, an agent configured to promote stress adaptation, and a nutrient at the agriculture site.

21. The method of claim 1, wherein generating values of the set of agronomic indices based upon the set of microbiome-associated features comprises returning a value of a sustainable productivity index indicating low fertility of the agriculture site, and wherein executing the action comprises applying a biodynamic soil with carbon sequestration capacity and comprising calcium in order to improve fertility of the agriculture site.

* * * * *